United States Patent
Arora

(10) Patent No.: US 11,865,186 B2
(45) Date of Patent: Jan. 9, 2024

(54) GENE THERAPY TREATMENT OF ATRIAL FIBRILLATION

(71) Applicant: Northwestern University, Evanston, IL (US)

(72) Inventor: Rishi Arora, Chicago, IL (US)

(73) Assignee: Northwestern University, Evanston, IL (US)

(*) Notice: Subject to any disclaimer, the term of this patent is extended or adjusted under 35 U.S.C. 154(b) by 6 days.

(21) Appl. No.: 16/752,406

(22) Filed: Jan. 24, 2020

(65) Prior Publication Data

US 2020/0237929 A1 Jul. 30, 2020

Related U.S. Application Data

(60) Provisional application No. 62/796,421, filed on Jan. 24, 2019.

(51) Int. Cl.

| | |
|---|---|
| *A61K 48/00* | (2006.01) |
| *C12N 15/79* | (2006.01) |
| *C07H 21/02* | (2006.01) |
| *C12N 15/113* | (2010.01) |
| *A61P 9/06* | (2006.01) |
| *C07K 14/47* | (2006.01) |
| *A61K 38/00* | (2006.01) |

(52) U.S. Cl.
CPC ............. *A61K 48/005* (2013.01); *A61P 9/06* (2018.01); *C07K 14/4703* (2013.01); *C12N 15/1137* (2013.01); *A61K 38/00* (2013.01)

(58) Field of Classification Search
CPC .... A61K 48/005; A61K 31/713; C12N 15/79; C12N 15/85; C12N 15/86; C12N 2310/14; C12N 2320/31; C07H 21/02; C07H 21/04

See application file for complete search history.

(56) References Cited

U.S. PATENT DOCUMENTS

| | | | |
|---|---|---|---|
| 6,559,128 B1 | 5/2003 | Hamm et al. | |
| 8,193,151 B2 | 6/2012 | Arora et al. | |
| 8,518,884 B2 | 8/2013 | Arora et al. | |
| 9,078,918 B2 | 7/2015 | Arora | |
| 9,932,588 B2 | 4/2018 | Arora | |
| 10,369,360 B2 | 8/2019 | Arora et al. | |
| 2003/0162258 A1 | 8/2003 | Hamm et al. | |
| 2007/0077597 A1 | 4/2007 | Gilchrist et al. | |
| 2007/0231830 A1 | 10/2007 | Gilchrist et al. | |
| 2008/0025958 A1 | 1/2008 | Hannon et al. | |
| 2013/0331432 A1 | 12/2013 | Stephanopoulos et al. | |
| 2015/0203852 A1 | 7/2015 | Arora | |
| 2017/0172440 A1 | 6/2017 | Arora | |
| 2021/0038501 A1 | 2/2021 | Arora et al. | |

FOREIGN PATENT DOCUMENTS

WO   WO 2005/078094   8/2005

OTHER PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Cruz et al., 2017, Methods in Molecular Biology, vol. 1654, Chapter 5, pp. 55-75.*
Yoo et al., 2013, Circulation, 2013: 128 A15234, p. 1-2.*
Aistrup et al., Targeted G-protein inhibition as a novel approach to decrease vagal atrial fibrillation by selective parasympathetic attenuation. Cardiovasc Res. Aug. 1, 2009;83(3):481-92.
Aistrup et al., Targeted nonviral gene-based inhibition of Galpha(i/o)-mediated vagal signaling in the posterior left atrium decreases vagal-induced atrial fibrillation. Heart Rhythm. Nov. 2011;8(11):1722-9.
Andrade et al., Efficacy and safety of cryoballoon ablation for atrial fibrillation: a systematic review of published studies. Heart Rhythm. Sep. 2011;8(9):1444-51.
Arora et al., Neural substrate for atrial fibrillation: implications for targeted parasympathetic blockade in the posterior left atrium. Am J Physiol Heart Circ Physiol. Jan. 2008;294(1):H134-44.
Arora et al., Recent insights into the role of the autonomic nervous system in the creation of substrate for atrial fibrillation: implications for therapies targeting the atrial autonomic nervous system. Circ Arrhythm Electrophysiol. Aug. 1, 2012;5(4):850-9.
Arora et al., Unique autonomic profile of the pulmonary veins and posterior left atrium. J Am Coll Cardiol. Mar. 27, 2007;49(12):1340-8.
Avitall et al., Atrial and ventricular fibrosis induced by atrial fibrillation: evidence to support early rhythm control. Heart Rhythm. Jun. 2008;5(6):839-45.
Bikou et al., Connexin 43 gene therapy prevents persistent atrial fibrillation in a porcine model. Cardiovasc Res. Nov. 1, 2011;92(2):218-25.
Boersma et al., Multielectrode Pulmonary Vein Isolation Versus Single Tip Wide Area Catheter Ablation for Paroxysmal Atrial Fibrillation: A Multinational Multicenter Randomized Clinical Trial. Circ Arrhythm Electrophysiol. Apr. 2016;9(4):e003151. 14 pages.

(Continued)

*Primary Examiner* — Shin Lin Chen
(74) *Attorney, Agent, or Firm* — David W. Staple

(57) ABSTRACT

Provided herein are compositions, methods, and devices for the treatment and prevention of atrial fibrillation (AF) using gene therapy techniques. In particular, oxidative stress (OS) and parasympathetic nervous system signaling are inhibited to prevent and/or reverse the electrical remodeling that underlies AF.

7 Claims, 10 Drawing Sheets

Specification includes a Sequence Listing.

(56) References Cited

OTHER PUBLICATIONS

Calkins et al., 2012 HRS/EHRA/ECAS Expert Consensus Statement on Catheter and Surgical Ablation of Atrial Fibrillation: recommendations for patient selection, procedural techniques, patient management and follow-up, definitions, endpoints, and research trial design. Europace. Apr. 2012;14(4):528-606.

Camm et al., Hopes and disappointments with antiarrhythmic drugs. Int J Cardiol. Jun. 15, 2017;237:71-74.

Chugh et al., Worldwide epidemiology of atrial fibrillation: a Global Burden of Disease 2010 Study. Circulation. Feb. 25, 2014;129(8):837-47.

Chung et al., Changes in ventricular remodelling and clinical status during the year following a single administration of stromal cell-derived factor-1 non-viral gene therapy in chronic ischaemic heart failure patients: the STOP-HF randomized Phase II trial. Eur Heart J. Sep. 1, 2015;36(33):2228-38.

Elbashir et al., Duplexes of ;21-nucleotide RNAs mediate RNA interference in cultured mammalian cells. Nature. May 24, 2001;411(6836):494-8.

Elbashir et al., RNA interference is mediated by 21—and 22-nucleotide RNAs. Genes Dev. Jan. 15, 2001;15(2):188-200.

Estner et al., Electrogram-guided substrate ablation with or without pulmonary vein isolation in patients with persistent atrial fibrillation. Europace. Nov. 2008;10(11):1281-7.

Ge et al., Effects of Chemical Modification on the Potency, Serum Stability, and Immunostimulatory Properties of Short shRNAs. RNA. Jan. 2010;16(1):118-30.

Ge et al., Minimal-length short hairpin RNAs: The Relationship of Structure and RNAi Activity. RNA. Jan. 2010;16(1):106-17.

GenBank Accession No. NM020988, downloaded Mar. 22, 2022. 5 pages.

Gillinov et al., Ablation of atrial fibrillation with concomitant cardiac surgery. Semin Thorac Cardiovasc Surg. Spring 2007;19(1):25-32.

Guerra et al., Intravenous vernakalant for the rapid conversion of recent onset atrial fibrillation: systematic review and meta-analysis. Expert Rev Cardiovasc Ther. Sep. 2014;12(9):1067-75.

Haissaguerre et al., Driver domains in persistent atrial fibrillation. Circulation. Aug. 12, 2014;130(7):530-8.

Hyde et al., CpG-free plasmids confer reduced inflammation and sustained pulmonary gene expression. Nat Biotechnol. May 2008;26(5):549-51.

Jaski et al., Calcium upregulation by percutaneous administration of gene therapy in cardiac disease (CUPID Trial), a first-in-human phase 1/2 clinical trial. J Card Fail. Apr. 2009;15(3):171-81.

Jessup et al., Calcium Upregulation by Percutaneous Administration of Gene Therapy in Cardiac Disease (CUPID): a phase 2 trial of intracoronary gene therapy of sarcoplasmic reticulum Ca2+-ATPase in paitents with advanced heart failure. Circulation. Jul. 19, 2011;124(3):304-13.

Kim et al., A myocardial Nox2 containing NAD(P)H oxidase contributes to oxidative stress in human atrial fibrillation. Circ Res. Sep. 30, 2005;97(7):629-36.

Kirchhof et al., Catheter ablation in patients with persistent atrial fibrillation. Eur Heart J. Jan. 1, 2017;38(1):20-26.

Koduri et al., Contribution of fibrosis and the autonomic nervous system to atrial fibrillation electrograms in heart failure. Circ Arrhythm Electrophysiol. Aug. 1, 2012;5(4):640-9.

Kunamalla et al., Constitutive Expression of a Dominant-Negative TGF-beta Type II Receptor in the Posterior Left Atrium Leads to Beneficial Remodeling of Atrial Fibrillation Substrate. Circ Res. Jun. 24, 2016;119(1):69-82.

Morrison et al., Pathophysiology of concomitant atrial fibrillation and heart failure: implications for management. Nat Clin Pract Cardiovasc Med. Jan. 2009;6(1):46-56.

Naccarelli et al., The role of dronedarone in the treatment of atrial fibrillation/flutter in the aftermath of PALLAS. Curr Cardiol Rev 2014;Curr Cardiol Rev. Nov. 2014;10(4):303-8.

Nademanee et al., A new approach for catheter ablation of atrial fibrillation: mapping of the electrophysiologic substrate. J Am Coll Cardiol. Jun. 2, 2004;43(11):2044-53.

Nademanee et al., Clinical outcomes of catheter substrate ablation for high-risk patients with atrial fibrillation. J Am Coll Cardiol. Feb. 26, 2008;51(8):843-9.

Narayan et al., Ablation of rotor and focal sources reduces late recurrence of atrial fibrillation compared with trigger ablation alone: extended follow-up of the CONFIRM trial (Conventional Ablation for Atrial Fibrillation With or Without Focal Impulse and Rotor Modulation). J Am Coll Cardiol 2014;63:1761-8.

NCBI Accession No. AAH30027, Jul. 25, 2016, 1 pg.

NCBI Accession No. ACN58588.1, Jul. 24, 2016, 2 pgs.

Ng et al., Autonomic remodeling in the left atrium and pulmonary veins in heart failure: creation of a dynamic substrate for atrial fibrillation. Circ Arrhythm Electrophysiol. Jun. 2011;4(3):388-96.

Page et al., Rhythm—and rate-controlling effects of dronedarone in patients with atrial fibrillation (from the ATHENA trial). Am J Cardiol. Apr. 1, 2011;107(7):1019-22.

Penn et al., An open-label dose escalation study to evaluate the safety of administration of nonviral stromal cell-derived factor-1 plasmid to treat symptomatic ischemic heart failure. Circ Res. Mar. 1, 2013;112(5):816-25.

Providencia et al., Higher contact-force values associated with better mid-term outcome of paroxysmal atrial fibrillation ablation using the SmartTouch catheter. Europace. Jan. 2015;17(1):56-63.

Rahman et al., Global epidemiology of atrial fibrillation. Nat Rev Cardiol. Nov. 2014;11(11):639-54.

Rahman et al., Global epidemiology of atrial fibrillation. Nat Rev Cardiol. Jul. 14, 2016;13(8):501.

Schotten et al., Pathophysiological mechanisms of atrial fibrillation: a translational appraisal. Physiol Rev. Jan. 2011;91(1):265-325.

Soucek et al., Genetic suppresson of atrial fibrillation using a dominant-negative ether-a-go-go-related gene mutant. Heart Rhythm. Feb. 2012;9(2):265-72.

Su et al., Nonviral gene therapy targeting cardiovascular system. Am J Physiol Heart Circ Physiol. Sep. 15, 2012;303(6):H629-38.

Trappe et al., Suppression of persistent atrial fibrillation by genetic knockdown of caspase 3: a pre-clinical pilot study. Eur Heart J. Jan. 2013;34(2):147-57.

Tuschl et al., Small interfering RNAs: a revolutionary tool for the analysis of gene function and gene therapy. Mol Interv. Jun. 2002;2(3):158-67.

Tuschl et al., Targeted mRNA degradation by double-stranded RNA in vitro. Genese Dev. Dec. 15, 1999;13(24):3191-7.

Ui-Tei et al., Thermodynamic stability and Watson-Crick base pairing in the seed duplex are major determinants of the efficiency of the siRNA-based off-target effect. Nucleic Acids Res. Dec. 2008;36(22):7100-9.

Ulphani et al., The ligament of Marshall as a parasympathetic conduit. Am J Physiol Heart Circ Physiol. Sep. 2007;293(3):H1629-35.

Wehr et al., Quantification of protein carbonylation. Methods Mol Biol. 2013;965:265-81.

Yoo et al., Disruption of NOX2-dependent Oxidative Injury with a Targeted Gene-Therapy Approach Prevents Atrial Fibrillation in a Canine Model., Preprint, Sep. 11, 2019, retrieved from: https://www.biorxiv.org/content/10.1101/765008v1.full.pdf, 57 pages.

Yoo et al., Selective inhibition of parasympathetic nerve signaling by novel C-terminal Gαi/0 peptides prevents electrical remodeling induced atrial fibrillation. Abstract PO02-88 from Poster Session II, Presented at Heart Rhythm 2013, San Francisco, CA, Thursday, May 5, 2016. Heart Rhythm 2016;13(5S):S200.

Zakkar et al., Inflammation, oxidative stress and postoperative atrial fibrillation in cardiac surgery. Pharmacol Ther. Oct. 2015;154:13-20.

Zsebo et al., Long-term effects of AAV1/SERVA2a gene transfer in patients with severe heart failure: analysis of recurrent cardiovascular events and mortality.Circ Res. Jan. 3, 2014;114(1):101-8.

International Search Report and Written Opionion for PCT/US2020/015063, dated Jun. 12, 2020, 15 pgs.

(56) References Cited

OTHER PUBLICATIONS

Dobrev et al. Molecular Basis of Downregulation of G-Protein-Coupled Inward Rectifying K+ Current (/ K,Ach ) in Chronic Human Atrial Fibrillation, Circulation, 2001:104(21):2551-2557.
European Extended Search Report for EO207444050.0, dated Apr. 5, 2023, 12 pgs.

* cited by examiner

A. PCR

B. Western blot

A. Scrambled gene

Atrial fibrillation

B. NOX2 shRNA

Atrial flutter          Atrial fibrillation

C. NOX2 shRNA + Gαi/o (Dog 1)

Atrial flutter

D. NOX2 shRNA + Gαi/o (Dog 2)

Conversion to sinus rhythm

FIG. 9

| NAME | AMINO ACID SEQUENCE | | | | | | | | | | | SEQ ID NO. |
|---|---|---|---|---|---|---|---|---|---|---|---|---|
| Gα$_t$ | M | G | I | K | E | N | L | K | D | C | G | L | F | 5 |
| Gα$_{t1/2}$ | M | G | I | K | N | N | L | K | D | C | G | L | F | 6 |
| Gα$_{t}$R | M | G | N | G | I | K | C | L | F | N | D | L | K | 7 |
| Gα$_{i3}$ | M | G | I | K | N | N | L | K | E | C | G | L | Y | 8 |
| Gα$_{o2}$ | M | G | I | A | K | N | L | R | G | C | G | L | Y | 9 |
| Gα$_{o1}$ | M | G | I | A | N | N | L | K | G | C | G | L | Y | 10 |
| Gα$_z$ | M | G | L | Q | L | N | L | K | Y | I | G | N | C | 11 |
| Gα$_{11}$ | M | G | L | Q | L | L | L | K | E | Y | N | L | V | 12 |
| Gα$_q$ | M | G | O | Q | M | N | L | K | E | Y | E | A | L | 13 |
| Gα$_{o14}$ | M | G | L | R | L | L | L | R | Q | F | N | L | V | 14 |
| Gα$_{14}$ | M | G | L | A | R | Y | L | D | E | I | M | L | L | 15 |
| Gα$_{15/16}$ | M | G | L | Q | E | N | L | K | B | I | N | L | V | 16 |
| Gα$_{12}$ | M | G | L | H | D | N | L | R | D | L | M | Q | Q | 17 |
| Gα$_{13}$ | M | G | L | R | M | H | L | R | Q | Y | E | L | Q | 18 |
| Gα$_s$ | M | G | Q | R | N | L | L | L | C | Q | E | L | L | 19 |

FIG. 10

| NUCLEOTIDE SEQUENCE | SEQ ID NO. |
|---|---|
| 5' gatccgccgccacc atg gga atc aag gaa aac ctg aag gac tgc ggc ctc ttc tgaa 3' | 20 |
| 5' gatccgccgccacc atg gga atc aag gaa aac ctg aag gac tgc ggc ctc ttc tgaa 3' | 21 |
| 5' gatccgccgccacc atg gga aac ggc atc aag tgc ctc ttc aac gac aag ctg tgaa 3' | 22 |
| 5' gatccgccgccacc atg gga att aaa aac tta aag gaa tgt gga ctt tat tgaa 3' | 23 |
| 5' gatccgccgccacc atg gga atc gcc aaa aac ctg cgg ggc tgt gga ctc tac tgaa 3' | 24 |
| 5' gatccgccgccacc atg gga att gcc aac aac ctc ggc ggc tgc ttg tac tgaa 3' | 25 |
| 5' gatccgccgccacc atg gga ata cag aat ctc aag tac att ggc ctt tgc tgaa 3' | 26 |
| 5' gatccgccgccacc atg gga ctg cag ctg aac ctg aag gag tac aat ctg gtc tgaa 3' | 27 |
| 5' gatccgccgccacc atg gga ctc cag ttg aac ctg aag gag tac aat gca gtc tgaa 3' | 28 |
| 5' gatccgccgccacc atg gga cag cgg atg cac ctc aag cag tat gag ctc ttg tgaa 3' | 29 |
| 5' gatccgccgccacc atg gga cta cag cta aac agg gaa ttc aac ctt gtc tgaa 3' | 30 |
| 5' gatccgccgccacc atg gga ctc gcc cgg tac ctg gac gag att aat ctg ctg tgaa 3' | 31 |
| 5' gatccgccgccacc atg gga ctg cag gag aac ctg aag gac atc atg ctg cag tgaa 3' | 32 |
| 5' gatccgccgccacc atg gga cag cag cgc atg ctt cgt cag cac tac gag ctc tgaa 3' | 33 |

SEQUENCE LISTING

<160> NUMBER OF SEQ ID NOS: 34

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tatccatttc caagtcatag g                                              21

<210> SEQ ID NO 2
<211> LENGTH: 7084
<212> TYPE: DNA
<213> ORGANISM: Artificial sequence
<220> FEATURE:
<223> OTHER INFORMATION: Synthetic

<400> SEQUENCE: 2

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga    600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa gtagtaaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agttttttgct gtactttcta tagtgaatag agttaggcag ggatattcac cattatcgtt    1680
tgagacccac ctcccaaccc cgaggggacc cgacaggccc gaaggaatag aagaagaagg    1740
tggagagaga gacagagaca gatccattcg attagtgaac ggatctcgac ggtatcgatc    1800
acgagactag cctcgagcgg ccgccccctt caccgagggc ctatttccca tgattccttc    1860
atatttgcat atacgataca aggctgttag agagataatt ggaattaatt tgactgtaaa    1920
cacaaagata ttagtacaaa atacgtgacg tagaaagtaa taatttcttg ggtagtttgc    1980
agttttaaaa ttatgtttta aaatggacta tcatatgctt accgtaactt gaaagtattt    2040
cgatttcttg gctttatata tcttgtggaa aggacgaaac accggtacaa cagccacaac    2100
gtctatctcg agatagacgt tgtggctgtt gtattttttga attctcgacc tcgagacaaa    2160
tggcagtatt catccacaat tttaaaagaa agggggggat tggggggtac agtgcagggg    2220
aaagaatagt agacataata gcaacagaca tacaaactaa agaattacaa aaacaaatta    2280
caaaaattca aaattttcgg gtttattaca gggacagcag agatccactt tggccgcggc    2340
```

```
tcgaggggt tggggttgcg ccttttccaa ggcagccctg ggtttgcgca gggacgcggc   2400
tgctctgggc gtggttccgg gaaacgcagc ggcgccgacc ctgggtctcg cacattcttc   2460
acgtccgttc gcagcgtcac ccggatcttc gccgctaccc ttgtgggccc cccggcgacg   2520
cttcctgctc cgcccctaag tcgggaaggt tccttgcggt tcgcggcgtg ccggacgtga   2580
caaacggaag ccgcacgtct cactagtacc ctcgcagacg gacagcgcca gggagcaatg   2640
gcagcgcgcc gaccgcgatg ggctgtggcc aatagcggct gctcagcagg gcgcgccgag   2700
agcagcggcc gggaaggggc ggtgcgggag gcggggtgtg gggcggtagt gtgggccctg   2760
ttcctgcccg cgcggtgttc cgcattctgc aagcctccgg agcgcacgtc ggcagtcggc   2820
tccctcgttg accgaatcac cgacctctct ccccaggggg atccaccgga gcttaccatg   2880
accgagtaca agcccacggt gcgcctcgcc accgcgacg acgtcccag ggccgtacgc   2940 accctcgccg ccgcgttcgc cgactacccc gccacgcgcc acaccgtcga tccggaccgc   3000
cacatcgagc gggtcaccga gctgcaagaa ctcttcctca cgcgcgtcgg gctcgacatc   3060
ggcaaggtgt gggtcgcgga cgacggcgcc gcggtggcgg tctggaccac gccggagagc   3120
gtcgaagcgg gggcggtgtt cgccgagatc ggcccgcgca tggccgagtt gagcggttcc   3180
cggctggccg agcagcaaca gatggaaggc ctcctggcgc cgcaccggcc caaggagccc   3240
gcgtggttcc tggccaccgt cggcgtctcg cccgaccacc agggcaaggg tctgggcagc   3300
gccgtcgtgc tccccggagt ggaggcggcc gagcgcgccg gggtgcccgc cttcctggag   3360
acctccgcgc ccgcaacct ccccttctac gagcggctcg gcttcaccgt caccgccgac   3420
gtcgaggtgc ccgaaggacc gcgcacctgg tgcatgaccc gcaagcccgg tgcctgacgc   3480
ccgccccacg accgcagcg cccgaccgaa aggagcgcac gacccatgc atcggtacct   3540 ttaagaccaa tgacttacaa ggcagctgta gatcttagcc acttttaaa agaaaagggg   3600 ggactggaag ggctaattca ctcccaacga agacaagatc tgcttttgc ttgtactggg   3660 tctctctggt tagaccagat ctgagcctgg gagctctctg gctaactagg gaacccactg   3720
cttaagcctc aataaagctt gccttgagtg cttcaagtag tgtgtgcccg tctgttgtgt   3780
gactctggta actagagatc cctcagaccc ttttagtcag tgtggaaaat ctctagcagt   3840
agtagttcat gtcatcttat tattcagtat ttataacttg caaagaaatg aatatcagag   3900
agtgagagga acttgtttat tgcagcttat aatggttaca aataaagcaa tagcatcaca   3960
aatttcacaa ataaagcatt ttttcactg cattctagtt gtggtttgtc caaactcatc   4020
aatgtatctt atcatgtctg gctctagcta tcccgcccct aactccgccc atcccgcccc   4080
taactccgcc cagttccgcc cattctccgc cccatggctg actaatttt tttatttatg   4140 cagaggccga ggccgcctcg gcctctgagc tattccagaa gtagtgagga ggcttttttg   4200
gaggcctagg gacgtaccca attcgcccta tagtgagtcg tattacgcgc gctcactggc   4260
cgtcgtttta caacgtcgtg actgggaaaa ccctggcgtt acccaactta atcgccttgc   4320
agcacatccc cctttcgcca gctggcgtaa tagcgaagag gcccgcaccg atcgcccttc   4380
ccaacagttg cgcagcctga atggcgaatg ggacgcgccc tgtagcggcg cattaagcgc   4440
ggcgggtgtg gtggttacgc gcagcgtgac cgctacactt gccagcgccc tagcgcccgc   4500
tcctttcgct ttcttccctt cctttctcgc cacgttcgcc ggctttcccc gtcaagctct   4560
aaatcggggg ctccctttag ggttccgatt tagtgcttta cggcacctcg accccaaaaa   4620
acttgattag ggtgatggtt cacgtagtgg gccatcgccc tgatagacgg ttttcgccc   4680
```

```
tttgacgttg gagtccacgt tctttaatag tggactcttg ttccaaactg gaacaacact    4740
caaccctatc tcggtctatt cttttgattt ataagggatt ttgccgattt cggcctattg    4800
gttaaaaaat gagctgattt aacaaaaatt taacgcgaat tttaacaaaa tattaacgct    4860
tacaatttag gtggcacttt tcggggaaat gtgcgcggaa cccctatttg tttattttc     4920 taaatacatt caaatatgta tccgctcatg agacaataac cctgataaat gcttcaataa    4980
tattgaaaaa ggaagagtat gagtattcaa catttccgtg tcgcccttat tcccttttt     5040 gcggcatttt gccttcctgt ttttgctcac ccagaaacgc tggtgaaagt aaaagatgct    5100
gaagatcagt tgggtgcacg agtgggttac atcgaactgg atctcaacag cggtaagatc    5160
cttgagagtt ttcgccccga agaacgtttt ccaatgatga gcacttttaa agttctgcta    5220
tgtggcgcgg tattatcccg tattgacgcc gggcaagagc aactcggtcg ccgcatacac    5280
tattctcaga atgacttggt tgagtactca ccagtcacag aaaagcatct tacggatggc    5340
atgacagtaa gagaattatg cagtgctgcc ataaccatga gtgataacac tgcggccaac    5400
ttacttctga caacgatcgg aggaccgaag gagctaaccg cttttttgca acatgggg      5460 gatcatgtaa ctcgccttga tcgttgggaa ccggagctga atgaagccat accaaacgac    5520
gagcgtgaca ccacgatgcc tgtagcaatg gcaacaacgt tgcgcaaact attaactggc    5580
gaactactta ctctagcttc ccggcaacaa ttaatagact ggatggaggc ggataaagtt    5640
gcaggaccac ttctgcgctc ggcccttccg gctggctggt ttattgctga taaatctgga    5700
gccggtgagc gtgggtctcg cggtatcatt gcagcactgg ggccagatgg taagccctcc    5760
cgtatcgtag ttatctacac gacggggagt caggcaacta tggatgaacg aaatagacag    5820
atcgctgaga taggtgcctc actgattaag cattggtaac tgtcagacca agtttactca    5880
tatatacttt agattgattt aaaacttcat ttttaattta aaaggatcta ggtgaagatc    5940 cttttttgata atctcatgac caaaatccct taacgtgagt tttcgttcca ctgagcgtca    6000
gaccccgtag aaaagatcaa aggatcttct tgagatcctt ttttctgcg  cgtaatctgc    6060 tgcttgcaaa caaaaaaacc accgctacca gcggtggttt gtttgccgga tcaagagcta    6120
ccaactcttt ttccgaaggt aactggcttc agcagagcgc agataccaaa tactgttctt    6180
ctagtgtagc cgtagttagg ccaccacttc aagaactctg tagcaccgcc tacatacctc    6240
gctctgctaa tcctgttacc agtggctgct gcagttggcg ataagtcgtg tcttaccggg    6300
ttggactcaa gacgatagtt accggataag gcgcagcggt cgggctgaac ggggggttcg    6360
tgcacacagc ccagcttgga gcgaacgacc tacaccgaac tgagatacct acagcgtgag    6420
ctatgagaaa gcgccacgct tcccgaaggg agaaaggcgg acaggtatca ggtaagcggc    6480
agggtcggaa caggagagcg cacgagggag cttccagggg gaaacgcctg gtatctttat    6540
agtcctgtcg ggtttcgcca cctctgactt gagcgtcgat ttttgtgatg ctcgtcaggg    6600
gggcggagcc tatggaaaaa cgccagcaac gcggcctttt tacggttcct ggccttttgc    6660
tggccttttg ctcacatgtt ctttcctgcg ttatcccctg attctgtgga taaccgtatt    6720
accgcctttg agtgagctga taccgctcgc cgcagccgaa cgaccgagcg cagcgagtca    6780
gtgagcgagg aagcggaaga gcgcccaata cgcaaaccgc ctctccccgc gcgttggccg    6840
attcattaat gcagctggca cgacaggttt cccgactgga aagcgggcag tgagcgcaac    6900
gcaattaatg tgagttagct cactcattag gcaccccagg ctttacactt tatgcttccg    6960
gctcgtatgt tgtgtggaat tgtgagcgga taacaatttc acacaggaaa cagctatgac    7020
catgattacg ccaagcgcgc aattaaccct cactaaaggg aacaaaagct ggagctgcaa    7080
```

```
gctt                                                                  7084
```

<210> SEQ ID NO 3
<211> LENGTH: 11
<212> TYPE: PRT
<213> ORGANISM: Artificial sequence
<220> FEATURE:
<223> OTHER INFORMATION: Synthetic
<400> SEQUENCE: 3

```
Ile Lys Asn Asn Leu Lys Asp Cys Gly Leu Phe
1               5                   10
```

<210> SEQ ID NO 4
<211> LENGTH: 11
<212> TYPE: PRT
<213> ORGANISM: Artificial sequence
<220> FEATURE:
<223> OTHER INFORMATION: Synthetic
<400> SEQUENCE: 4

```
Ile Ala Asn Asn Leu Arg Gly Cys Gly Leu Tyr
1               5                   10
```

<210> SEQ ID NO 5
<211> LENGTH: 13
<212> TYPE: PRT
<213> ORGANISM: Artificial sequence
<220> FEATURE:
<223> OTHER INFORMATION: Synthetic
<400> SEQUENCE: 5

```
Met Gly Ile Lys Glu Asn Leu Lys Asp Cys Gly Leu Phe
1               5                   10
```

<210> SEQ ID NO 6
<211> LENGTH: 13
<212> TYPE: PRT
<213> ORGANISM: Artificial sequence
<220> FEATURE:
<223> OTHER INFORMATION: Synthetic
<400> SEQUENCE: 6

```
Met Gly Ile Lys Asn Asn Leu Lys Asp Cys Gly Leu Phe
1               5                   10
```

<210> SEQ ID NO 7
<211> LENGTH: 13
<212> TYPE: PRT
<213> ORGANISM: Artificial sequence
<220> FEATURE:
<223> OTHER INFORMATION: Synthetic
<400> SEQUENCE: 7

```
Met Gly Asn Gly Ile Lys Cys Leu Phe Asn Asp Lys Leu
1               5                   10
```

<210> SEQ ID NO 8
<211> LENGTH: 13
<212> TYPE: PRT
<213> ORGANISM: Artificial sequence
<220> FEATURE:
<223> OTHER INFORMATION: Synthetic
<400> SEQUENCE: 8

```
Met Gly Ile Lys Asn Asn Leu Lys Glu Cys Gly Leu Tyr
```

```
1               5                   10
```

<210> SEQ ID NO 9
<211> LENGTH: 13
<212> TYPE: PRT
<213> ORGANISM: Artificial sequence
<220> FEATURE:
<223> OTHER INFORMATION: Synthetic

<400> SEQUENCE: 9

```
Met Gly Ile Ala Lys Asn Leu Arg Gly Cys Gly Leu Tyr
1               5                   10
```

<210> SEQ ID NO 10
<211> LENGTH: 13
<212> TYPE: PRT
<213> ORGANISM: Artificial sequence
<220> FEATURE:
<223> OTHER INFORMATION: Synthetic

<400> SEQUENCE: 10

```
Met Gly Ile Ala Asn Asn Leu Arg Gly Cys Gly Leu Tyr
1               5                   10
```

<210> SEQ ID NO 11
<211> LENGTH: 13
<212> TYPE: PRT
<213> ORGANISM: Artificial sequence
<220> FEATURE:
<223> OTHER INFORMATION: Synthetic

<400> SEQUENCE: 11

```
Met Gly Ile Gln Asn Asn Leu Lys Tyr Ile Gly Leu Cys
1               5                   10
```

<210> SEQ ID NO 12
<211> LENGTH: 13
<212> TYPE: PRT
<213> ORGANISM: Artificial sequence
<220> FEATURE:
<223> OTHER INFORMATION: Synthetic

<400> SEQUENCE: 12

```
Met Gly Leu Gln Leu Asn Leu Lys Glu Tyr Asn Leu Val
1               5                   10
```

<210> SEQ ID NO 13
<211> LENGTH: 13
<212> TYPE: PRT
<213> ORGANISM: Artificial sequence
<220> FEATURE:
<223> OTHER INFORMATION: Synthetic

<400> SEQUENCE: 13

```
Met Gly Leu Gln Leu Asn Leu Lys Glu Tyr Asn Ala Val
1               5                   10
```

<210> SEQ ID NO 14
<211> LENGTH: 13
<212> TYPE: PRT
<213> ORGANISM: Artificial sequence
<220> FEATURE:
<223> OTHER INFORMATION: Synthetic

<400> SEQUENCE: 14

```
Met Gly Gln Arg Met His Leu Lys Gln Tyr Glu Leu Leu
1               5                   10
```

```
<210> SEQ ID NO 15
<211> LENGTH: 13
<212> TYPE: PRT
<213> ORGANISM: Artificial sequence
<220> FEATURE:
<223> OTHER INFORMATION: Synthetic

<400> SEQUENCE: 15

Met Gly Leu Gln Leu Asn Leu Arg Glu Phe Asn Leu Val
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthetic

<400> SEQUENCE: 16

Met Gly Leu Ala Arg Tyr Leu Asp Glu Ile Asn Leu Leu
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic

<400> SEQUENCE: 17

Met Gly Leu Gln Glu Asn Leu Lys Asp Ile Met Leu Gln
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic

<400> SEQUENCE: 18

Met Gly Leu His Asp Asn Leu Lys Gln Leu Met Leu Gln
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic

<400> SEQUENCE: 19

Met Gly Gln Arg Met His Leu Arg Gln Tyr Glu Leu Leu
1               5                   10

<210> SEQ ID NO 20
<211> LENGTH: 57
<212> TYPE: DNA
<213> ORGANISM: Artificial sequence
<220> FEATURE:
<223> OTHER INFORMATION: Synthetic

<400> SEQUENCE: 20
gatccgccgc caccatggaa atcaaggaaa acctgaagga ctgcggcctc ttctgaa      57
```

<210> SEQ ID NO 21
<211> LENGTH: 57
<212> TYPE: DNA
<213> ORGANISM: Artificial sequence
<220> FEATURE:
<223> OTHER INFORMATION: Synthetic

<400> SEQUENCE: 21
gatccgccgc caccatggga atcaagaaca acctgaagga ctgcggcctc ttctgaa    57

<210> SEQ ID NO 22
<211> LENGTH: 57
<212> TYPE: DNA
<213> ORGANISM: Artificial sequence
<220> FEATURE:
<223> OTHER INFORMATION: Synthetic

<400> SEQUENCE: 22
gatccgccgc caccatggga aacggcatca agtgcctctt caacgacaag ctgtgaa    57

<210> SEQ ID NO 23
<211> LENGTH: 57
<212> TYPE: DNA
<213> ORGANISM: Artificial sequence
<220> FEATURE:
<223> OTHER INFORMATION: Synthetic

<400> SEQUENCE: 23
gatccgccgc caccatggga attaaaaaca acttaaagga atgtggactt tattgaa    57

<210> SEQ ID NO 24
<211> LENGTH: 57
<212> TYPE: DNA
<213> ORGANISM: Artificial sequence
<220> FEATURE:
<223> OTHER INFORMATION: Synthetic

<400> SEQUENCE: 24
gatccgccgc caccatggga atcgccaaaa acctgcgggg ctgtggactc tactgaa    57

<210> SEQ ID NO 25
<211> LENGTH: 57
<212> TYPE: DNA
<213> ORGANISM: Artificial sequence
<220> FEATURE:
<223> OTHER INFORMATION: Synthetic

<400> SEQUENCE: 25
gatccgccgc caccatggga attgccaaca acctccgggg ctgcggcttg tactgaa    57

<210> SEQ ID NO 26
<211> LENGTH: 57
<212> TYPE: DNA
<213> ORGANISM: Artificial sequence
<220> FEATURE:
<223> OTHER INFORMATION: Synthetic

<400> SEQUENCE: 26
gatccgccgc caccatggga atacagaaca atctcaagta cattggcctt tgctgaa    57

<210> SEQ ID NO 27
<211> LENGTH: 57
<212> TYPE: DNA
<213> ORGANISM: Artificial sequence
<220> FEATURE:
<223> OTHER INFORMATION: Synthetic

<400> SEQUENCE: 27
gatccgccgc caccatggga ctgcagctga acctgaagga gtacaatctg gtctgaa    57

<210> SEQ ID NO 28
<211> LENGTH: 57
<212> TYPE: DNA
<213> ORGANISM: Artificial sequence
<220> FEATURE:
<223> OTHER INFORMATION: Synthetic

<400> SEQUENCE: 28
gatccgccgc caccatggga ctccagttga acctgaagga gtacaatgca gtctgaa    57

<210> SEQ ID NO 29
<211> LENGTH: 57
<212> TYPE: DNA
<213> ORGANISM: Artificial sequence
<220> FEATURE:
<223> OTHER INFORMATION: Synthetic

<400> SEQUENCE: 29
gatccgccgc caccatggga cagcggatgc acctcaagca gtatgagctc ttgtgaa    57

<210> SEQ ID NO 30
<211> LENGTH: 57
<212> TYPE: DNA
<213> ORGANISM: Artificial sequence
<220> FEATURE:
<223> OTHER INFORMATION: Synthetic

<400> SEQUENCE: 30
gatccgccgc caccatggga ctacagctaa acctaaggga attcaacctt gtctgaa    57

<210> SEQ ID NO 31
<211> LENGTH: 57
<212> TYPE: DNA
<213> ORGANISM: Artificial sequence
<220> FEATURE:
<223> OTHER INFORMATION: Synthetic

<400> SEQUENCE: 31
gatccgccgc caccatggga ctcgcccggt acctggacga gattaatctg ctgtgaa    57

<210> SEQ ID NO 32
<211> LENGTH: 57
<212> TYPE: DNA
<213> ORGANISM: Artificial sequence
<220> FEATURE:
<223> OTHER INFORMATION: Synthetic

<400> SEQUENCE: 32
gatccgccgc caccatggga ctgcaggaga acctgaagga catcatgctg cagtgaa    57

<210> SEQ ID NO 33
<211> LENGTH: 57
<212> TYPE: DNA
<213> ORGANISM: Artificial sequence
<220> FEATURE:
<223> OTHER INFORMATION: Synthetic

<400> SEQUENCE: 33
gatccgccgc caccatggga cagcgcatgc accttcgtca gtacgagctg ctgtgaa    57

<210> SEQ ID NO 34
<211> LENGTH: 57

```
<212> TYPE: DNA
<213> ORGANISM: Artificial sequence
<220> FEATURE:
<223> OTHER INFORMATION: Synthetic

<400> SEQUENCE: 34
ccgcctatga cttggaaatg gatactcgag tatccatttc caagtcatag gtttttg        57
```

GENE THERAPY TREATMENT OF ATRIAL FIBRILLATION

CROSS-REFERENCE TO RELATED APPLICATION

The present application claims priority to U.S. Provisional Patent Application Ser. No. 62/796,421, filed Jan. 24, 2019, which is hereby incorporated by reference in its entirety.

FIELD

Provided herein are compositions, methods, and devices for the treatment and prevention of atrial fibrillation (AF) using gene therapy techniques. In particular, oxidative stress (OS) and parasympathetic nervous system signaling are inhibited to prevent and/or reverse the electrical remodeling that underlies AF.

BACKGROUND

Atrial fibrillation (AF) is the most common heart rhythm disorder. It affects >6 million Americans and is a major cause of stroke. Since AF is primarily an age-related disease, it is fast becoming an epidemic in an aging population. Unfortunately, current therapies for AF—both pharmacological and ablation-based—are sub-optimal in patients with persistent AF. Ablation—considered the 'gold standard' in AF treatment today, is moderately successful (70-75% efficacy) in patients with paroxysmal AF (Ref. 1; herein incorporated by reference in its entirety), but has suboptimal efficacy (<50%) in persistent AF (refs. 2-4; herein incorporated by reference in their entireties).

NADPH oxidase 2 (Nox2), also known as cytochrome b (558) subunit beta or Cytochrome b-245 heavy chain, is a protein that in humans is encoded by the NOX2 gene (also called CYBB gene).[5] The protein is a super-oxide generating enzyme which forms reactive oxygen species (ROS).

$G_i$ protein alpha subunit is a family of heterotrimeric G protein alpha subunits. This family is also commonly called the $G_{i/o}$ ($G_i/G_o$) family or $G_{i/o/z/t}$ family to include closely related family members. G alpha subunits may be referred to as $G_i$ alpha, $G_{\alpha i}$, or $G_i\alpha$.

SUMMARY

Provided herein are compositions, methods, and devices for the treatment and prevention of atrial fibrillation (AF) using gene therapy techniques. In particular, oxidative stress (OS) and parasympathetic nervous system signaling are inhibited to prevent and/or reverse the electrical remodeling that underlies AF.

In some embodiments, provided herein are methods of treating atrial fibrillation (AF) comprising inhibiting/reducing oxidative stress (OS) and parasympathetic nervous system signaling by gene therapy approach. In some embodiments, the gene therapy approach comprises administration of transgenes to a subject suffering from or at risk of AF. In some embodiments, the gene therapy approach comprises administration of a NOX2 shRNA and/or one or both of $G\alpha_{i2}$ and $G\alpha_{o1}$ inhibitory peptides. In some embodiments, the gene therapy approach comprises electroporation.

In some embodiments, provided herein are methods of preventing or reversing cardiac electrical remodeling and/or atrial fibrillation in a subject, comprising administering an effective amount of: (a) a NADPH oxidase 2 (NOX2) inhibitor agent; and/or (b) (i) a $G\alpha_i$ inhibitory peptide, and/or (ii) a $G\alpha_o$ inhibitory peptide; to the subject, wherein said administering is under conditions such that a level of cardiac electrical remodeling and/or atrial fibrillation is prevented, reduced, or eliminated. In some embodiments, the NOX2 inhibitor agent is a nucleic acid inhibitor of NOX2 gene expression. In some embodiments, the nucleic acid inhibitor of NOX2 gene expression is a NOX2 siRNA. In some embodiments, the nucleic acid inhibitor of NOX2 gene expression is a NOX2 shRNA. In some embodiments, the NOX2 shRNA comprises at least 50% (e.g., 50%, 55%, 60%, 65%, 70%, 75%, 80%, 85%, 90%, 95%, 100%, or ranges therebetween) sequence identity with SEQ ID NO: 34. In some embodiments, the NOX2 shRNA is provided on a vector comprising at least 50% (e.g., 50%, 55%, 60%, 65%, 70%, 75%, 80%, 85%, 90%, 95%, 100%, or ranges therebetween) sequence identity with SEQ ID NO: 2. In some embodiments, the $G\alpha_i$ inhibitory peptide is a $G\alpha_{i2}$ inhibitory peptide. In some embodiments, the $G\alpha_i$ inhibitory peptide is a C-terminal $G\alpha_i$ inhibitory peptide. In some embodiments, the $G\alpha_o$ inhibitory peptide is a $G\alpha_{o1}$ inhibitory peptide. In some embodiments, the $G\alpha_o$ inhibitory peptide is a C-terminal $G\alpha_o$ inhibitory peptide. In some embodiments, the $G\alpha_i$ inhibitory peptide and/or the $G\alpha_o$ inhibitory peptide is administered as and expressed from a minigene. In some embodiments, the minigene is present on a plasmid. In some embodiments, the $G\alpha_i$ inhibitory peptide comprises at least 50% (e.g., 50%, 55%, 60%, 65%, 70%, 75%, 80%, 85%, 90%, 95%, 100%, or ranges therebetween) sequence identity with SEQ ID NO: 3. In some embodiments, the $G\alpha_o$ inhibitory peptide comprises at least 50% (e.g., 50%, 55%, 60%, 65%, 70%, 75%, 80%, 85%, 90%, 95%, 100%, or ranges therebetween) sequence identity with SEQ ID NO: 4. In some embodiments, the $G\alpha_i$ inhibitory peptide and the $G\alpha_o$ inhibitory peptide are co-administered. In some embodiments, the $G\alpha_i$ inhibitory peptide and the $G\alpha_o$ inhibitory peptide are co-administered at a ratio between 1:10 and 10:1 (e.g., 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or ranges therebetween). In some embodiments, the NOX2 inhibitor agent is co-administered with the $G\alpha_i$ inhibitory peptide and/or the $G\alpha_o$ inhibitory peptide. In some embodiments, the NOX2 inhibitor agent, the $G\alpha_i$ inhibitory peptide, and the $G\alpha_o$ inhibitory peptide are co-administered. In some embodiments, the NOX2 inhibitor agent, the $G\alpha_i$ inhibitory peptide, and/or the $G\alpha_o$ inhibitory peptide are administered to the myocardial tissue. In some embodiments, methods further comprise electroporating the tissue before, during, or after the administration. In some embodiments, the myocardial tissue comprises at least one of atrial tissue or ventricle tissue. In some embodiments, the NOX2 inhibitor agent, the $G\alpha_i$ inhibitory peptide, and/or the $G\alpha_o$ inhibitory peptide are administered to the endocardium or epicardium. In some embodiments, the NOX2 inhibitor agent, the $G\alpha_i$ inhibitory peptide, and/or the $G\alpha_o$ inhibitory peptide are administered to a segment of the coronary vasculature of the subject and target coronary tissue of the subject is electroporated. In some embodiments, administering an effective amount of the NOX2 inhibitor agent, $G\alpha_i$ inhibitory peptide, and/or the $G\alpha_o$ inhibitory peptide to the subject comprises administering an isolated therapeutic DNA that encodes and expresses the NOX2 inhibitor agent, $G\alpha_i$ inhibitory peptide, and/or the $G\alpha_o$ inhibitory peptide. In some embodiments, administering an effective amount of the NOX2 inhibitor agent, $G\alpha_i$ inhibitory peptide, and/or the $G\alpha_o$ inhibitory peptide to the subject comprises injecting the isolated therapeutic DNA. In some embodiments, the subject suffers from one or more of trial or ventricular arrhythmias, ventricular failure, or heart failure. In some embodiments, arrhythmia comprises atrial fibrillation.

In some embodiments, provided herein are pharmaceutical compositions comprising: (a) a NADPH oxidase 2 (NOX2) inhibitor agent; and (b) (i) a $G\alpha_i$ inhibitory peptide or nucleic acid encoding a $G\alpha_i$ inhibitory peptide, and/or (ii) a $G\alpha_o$ inhibitory peptide or nucleic acid encoding a $G\alpha_o$ inhibitory peptide. In some embodiments, the NOX2 inhibitor agent is a nucleic acid inhibitor of NOX2 gene expression. In some embodiments, the nucleic acid inhibitor of NOX2 gene expression is a NOX2 siRNA. In some embodiments, the nucleic acid inhibitor of NOX2 gene expression is a NOX2 shRNA. In some embodiments, the NOX2 shRNA comprises at least 50% (e.g., 50%, 55%, 60%, 65%, 70%, 75%, 80%, 85%, 90%, 95%, 100%, or ranges therebetween) sequence identity with SEQ ID NO: 34. In some embodiments, the NOX2 shRNA is provided on a vector comprising at least 50% (e.g., 50%, 55%, 60%, 65%, 70%, 75%, 80%, 85%, 90%, 95%, 100%, or ranges therebetween) sequence identity with SEQ ID NO: 2. In some embodiments, the $G\alpha_i$ inhibitory peptide is a $G\alpha_{i2}$ inhibitory peptide. In some embodiments, the $G\alpha_i$ inhibitory peptide is a C-terminal $G\alpha_i$ inhibitory peptide. In some embodiments, the $G\alpha o$ inhibitory peptide is a $G\alpha_{o1}$ inhibitory peptide. In some embodiments, the $G\alpha_o$ inhibitory peptide is a C-terminal $G\alpha_o$ inhibitory peptide. In some embodiments, the nucleic acid encoding a $G\alpha_o$ inhibitory peptide comprises a minigene. In some embodiments, the nucleic acid encoding a $G\alpha_o$ inhibitory peptide is a plasmid. In some embodiments, the nucleic acid encoding a $G\alpha_i$ inhibitory peptide comprises a minigene. In some embodiments, the nucleic acid encoding a $G\alpha_i$ inhibitory peptide is a plasmid. In some embodiments, the $G\alpha_i$ inhibitory peptide comprises at least 50% (e.g., 50%, 55%, 60%, 65%, 70%, 75%, 80%, 85%, 90%, 95%, 100%, or ranges therebetween) sequence identity with SEQ ID NO: 3. In some embodiments, the $G\alpha_o$ inhibitory peptide comprises at least 50% (e.g., 50%, 55%, 60%, 65%, 70%, 75%, 80%, 85%, 90%, 95%, 100%, or ranges therebetween) sequence identity with SEQ ID NO: 4. In some embodiments, the pharmaceutical composition comprises both the $G\alpha_i$ inhibitory peptide and the $G\alpha_o$ inhibitory peptide. In some embodiments, the pharmaceutical composition comprises both the nucleic acid encoding a $G\alpha_i$ inhibitory peptide and the nucleic acid encoding a $G\alpha_o$ inhibitory peptide. In some embodiments, the $G\alpha_i$ inhibitory peptide or/and nucleic acid encoding a $G\alpha_i$ inhibitory peptide and the $G\alpha_o$ inhibitory peptide or/and nucleic acid encoding a $G\alpha_o$ inhibitory peptide are present at a ratio between 1:10 and 10:1 (e.g., 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or ranges therebetween).

BRIEF DESCRIPTION OF THE DRAWINGS

FIG. 9. Exemplary amino acid sequences of modified carboxy terminal G$\alpha$ peptides.

FIG. 10. Nucleotide sequences of exemplary minigenes of the invention.

DEFINITIONS

Figure 1:
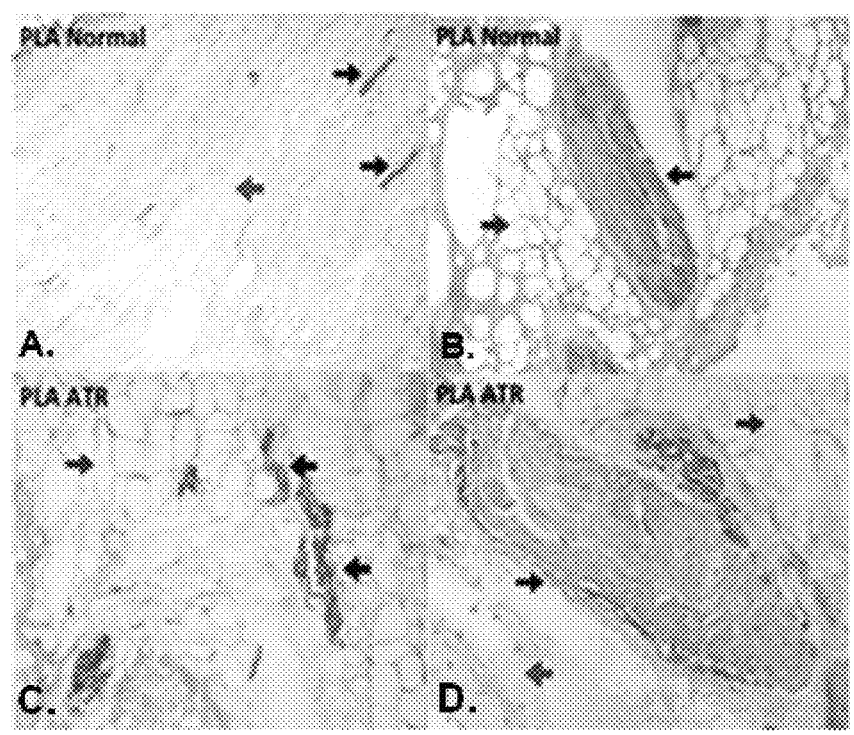
FIG. 1. RAP leads to nerve hypertrophy and increased sprouting of parasympathetic fibers.
Figure 1:
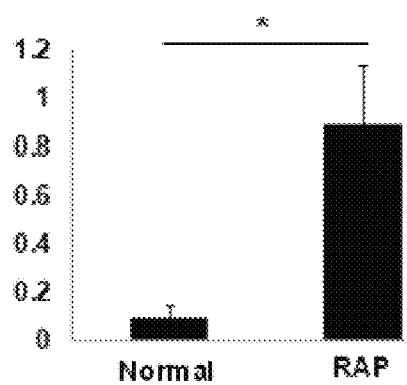
Figure 1:
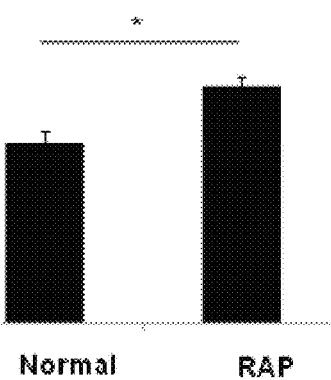

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a minigene" is a reference to one or more minigenes and equivalents thereof known to those skilled in the art, and so forth.

As used herein, the term "about," when referring to a value is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" refers to any animal including, but not limited to, insects, humans, non-human primates, vertebrates, bovines, equines, felines, canines, pigs, rodents, and the like. The terms "subject" and "patient" may be used interchangeably. A subject may be of any stage of life (e.g. embryo, fetus, infant, neonatal, child, adult, etc.). A subject may be male or female.

As used herein, the terms "treat," "treatment," and "treating" refer to reducing the amount or severity of a particular condition, disease state (e.g., cardiovascular disorder), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the term "treat," and linguistic variations thereof, encompasses therapeutic measures, while the term "prevent" and linguistic variations thereof, encompasses prophylactic measures, unless otherwise indicated.

The phrase "small hairpin RNA" and the term "shRNA", as used herein, refer to a unimolecular RNA-containing polynucleotide that is capable of performing RNAi and that includes a sense sequence, a loop, and an antisense sequence. The sense and antisense sequences are sometimes referred to herein as the first region and second region. As described herein, the sense and antisense sequences can be in different orientations with respect to one another in an shRNA of the invention (an L or R shRNA). Thus, if the first region of an shRNA is the sense sequence then the second region is the antisense region, and vice versa. Preferably, the sense and antisense sequences are substantially complementary to each other (about 80% complementary). The antisense sequence can be about 16 to about 22 nucleotides in length, e.g., about 16 to 19 nucleotides, and more preferably 18 to 19 nucleotides in length. The sense sequence can be about 11 to about 22 nucleotides in length, and more preferably 17 to 19 nucleotides in length. An shRNA (and other RNAi agents) are "specific" for a target gene when the antisense sequence (of about 16 to 22 nucleotides is substantially complementary to the target gene (or target RNA, e.g., target mRNA). By substantially complementary is meant that the antisense sequence is at least 80% complementary to the target gene (or gene product). Thus, in some embodiments, the antisense sequence that is complementary to the target gene can contain mismatches to the target. The sequence can be varied to target one or more genetic variants or phenotypes of a target, e.g., a viral target, by altering the targeting sequence to be complementary to the sequence of the genetic variant or phenotype. An shRNA may have a loop as long as, for example, 0 to about 24 nucleotides in length, preferably 0 to about 10 nucleotides in length, 0 to 6 nucleotides in length, e.g., 2 nucleotides in length. The sequence of the loop can include nucleotide residues unrelated to the target. In one particularly preferred embodiment, the loop is 5'-UU-3'. In some embodiments it may include non-nucleotide moieties. In yet other embodiments, the loop does not include any non-nucleotides moieties. Optionally, the shRNA can have an overhang region of 2 bases on 3' end of the molecule. The shRNA can also comprise RNAs with stem-loop structures that contain mismatches and/or bulges. The sense sequence that is homologous to the target can differ at about 0 to about 5 sites by having mismatches, insertions, or deletions of from about 1 to about 5 nucleotides, as is the case, for example, with naturally occurring microRNAs. RNAs that comprise any of the above structures can include structures where the loops comprise nucleotides, non-nucleotides, or combinations of nucleotides and non-nucleotides.

Additionally, the phrase "small hairpin RNA" and the term "shRNA" include nucleic acids that also contain moieties other than ribonucleotide moieties, including, but not limited to, modified nucleotides, modified internucleotide linkages, non-nucleotides, deoxynucleotides and analogs of the nucleotides mentioned thereof. Description of modified shRNAs of interest can be found in the following references, both of which are incorporated herein by reference in their entirety: Q. Ge, H. Ilves, A. Dallas, P. Kumar, J. Shorenstein, S. A. Kazakov, and B. H. Johnston (2010) Minimal-length short hairpin RNAs: The Relationship of Structure and RNAi Activity. RNA 16(1):106-17 (Epub Dec. 1, 2009); and Q. Ge, A. Dallas, H. Ilves, J. Shorenstein, M. A. Behlke, and B. H. Johnston (2010) Effects of Chemical Modification on the Potency, Serum Stability, and Immunostimulatory Properties of Short shRNAs. RNA 16(1):118-30 (Epub Nov. 30, 2009).

The phrase "antisense sequence", as used herein, refers to a polynucleotide or region of a polynucleotide that is substantially complementary (e.g., 80% or more) or 100% complementary to a target nucleic acid of interest. An antisense sequence can be composed of a polynucleotide region that is RNA, DNA or chimeric RNA/DNA. Any nucleotide within an antisense sequence can be modified by including substituents coupled thereto, such as in a 2' modification. The antisense sequence can also be modified with a diverse group of small molecules and/or conjugates. For example, an antisense sequence may be complementary, in whole or in part, to a molecule of messenger RNA, an RNA sequence that is not mRNA (e.g., tRNA, rRNA, hnRNA, negative and positive stranded viral RNA and its complementary RNA) or a sequence of DNA that is either coding or non-coding.

The phrase "sense sequence", as used herein, refers to a polynucleotide or region that has the same nucleotide sequence, in whole or in part, as a target nucleic acid such as a messenger RNA or a sequence of DNA. When a sequence is provided, by convention, unless otherwise indicated, it is the sense sequence (or region), and the presence of the complementary antisense sequence (or region) is implicit.

The term "complementary", as used herein, refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes.

"Perfect complementarity" or "100% complementarity", as used herein, refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 19-mers, if 17 base pairs on each strand or each region can hydrogen bond with each other, the polynucleotide strands exhibit 89.5% complementarity. Substantial complementarity refers to polynucleotide strands or regions exhibiting about 80% or greater complementarity.

As used herein, the term "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion or as described elsewhere throughout the specification.

The phrase "pharmaceutically acceptable carrier", as used herein, means a pharmaceutically acceptable salt, solvent, suspending agent or vehicle for delivering a composition of the present disclosure to the animal or human. The carrier may be liquid, semisolid or solid, and is often synonymously used with diluent, excipient or salt. The phrase "pharmaceutically acceptable" means that an ingredient, excipient, carrier, diluent or component disclosed is one that is suitable for use with humans and/or animals without undue adverse side effects (such as toxicity, irritation, and allergic response) commensurate with a reasonable benefit/risk ratio. See Remington's Pharmaceutical Sciences 16.sup.th edition, Osol, A. Ed (1980) (incorporated herein by reference in its entirety).

As used herein the term "minigene" refers to a minimal gene fragment that excludes one or more components of a native gene locus but includes the necessary elements for expression of the gene product or some portion of the gene product or a synthetic construct.

DETAILED DESCRIPTION

A major reason for the failure of current therapies is that they are not targeted at key molecular mechanisms underlying AF and therefore do not arrest the underlying disease process. AF is a multi-factorial disease with several key underlying molecular mechanisms. Since current drugs and ablation are not targeted at key molecular mechanisms, they do not arrest the underlying disease process.

Experiments conducted during development of embodiments herein demonstrate that NOX2 shRNA entirely prevents rapid atrial pacing (RAP) induced electrical remodeling and AF. NOX2 shRNA can also prevent atrial fibrosis in a HF model. Parasympathetic inhibition (with Gαi/o-ct) also significantly attenuated RAP induced electrical remodeling and AF. NOX2 shRNA attenuated parasympathetic nerve sprouting in dogs undergoing RAP, indicating a significant interaction between oxidative injury and parasympathetic signaling in creation of electrical remodeling in AF. Furthermore, experiments demonstrated that NOX2 shRNA was able to reverse electrical remodeling in RAP dogs with established AF, especially when given in combination with Gαi/o-ct.

Provided herein are approaches to the treatment and prevention of AF that target one or more major molecular mechanisms underlying development of the AF disease state. Certain embodiments herein target fundamental mechanisms that contribute to electrical remodeling in AF (e.g., oxidative stress (OS), parasympathetic nervous system signaling, etc.). In some embodiments, provided herein are gene therapy approaches to inhibit OS and parasympathetic signaling in one or both atria. In some embodiments, by directly targeting two key molecular mechanisms underlying electrical remodeling in AF, the approach decreases AF in patients resistant to ablation.

In some embodiments, provided herein is direct atrial injection of transgene(s) targeted to OS and/or parasympathetic signaling, to reverse established substrate for AF. In some embodiments, the gene targeted to OS is NOX2 shRNA. In some embodiments, the genes targeted to parasympathetic signaling include one or both of $G\alpha_{i2}$ and $G\alpha_{o1}$ inhibitory peptides. Experiments conducted during development of embodiments herein indicate that both NOX2 shRNA and $G\alpha_{i2}/G\alpha_{o1}$ peptides prevent electrical remodeling in a rapid atrial pacing (RAP) canine model of AF, with a resulting decrease in AF. Experiments conducted during development of embodiments herein also indicate that these mechanisms are closely inter-related, with OS contributing to electrical remodeling in AF at least in part by causing parasympathetic nerve hypertrophy/sprouting in the atrium. In some embodiments, the capacity of the present approaches herein to reverse established AF substrate provides the therapeutic action of the technology. In some embodiments, embodiments herein modify the AF disease state, restore sinus rhythm, and lead to a decrease in AF related stroke, heart failure, etc.

In some embodiments, the treatment is administered epicardially by surgeons during open-heart surgery for coronary bypass or valve replacement. In some embodiments, a less invasive transvenous endocardial approach is utilized.

Experiments conducted during development of embodiments herein have identified fundamental mechanisms in the creation of the atrial fibrillation (AF) disease state (Ref. 8-10; herein incorporated by reference in their entireties) and identified several trans-genes that can selectively target these mechanisms in the atrium (Ref. 10-11; herein incorporated by reference in their entireties). Some embodiments herein target in combination two fundamental mechanisms that contribute to electrical remodeling in AF, oxidative stress and parasympathetic nervous system signaling. In some embodiments, vectors (e.g., plasmids) expressing the following trans-genes are used: (a) NOX2 shRNA (this gene inhibits NOX2, a major enzymatic source of oxidative stress), and (b) C-terminal $G\alpha_i+G\alpha_o$ inhibitory peptides (e.g., 1:1 ratio) (these inhibit parasympathetic atrial signaling). In some embodiments, a therapeutic comprises NOX2 shRNA±($G\alpha_i+G\alpha_o$ plasmids).

Experiments were conducted during development of embodiments herein that demonstrate that the transgenes (plasmids) are successfully expressed in the atrium by using electroporation, with a resulting decrease in AF in a clinically relevant large animal model of AF. The efficacy of the approach in preventing electrical remodeling in AF is described below. Experiments are conducted during development of embodiments herein to demonstrate that the trans-genes reverse established AF substrate. Since the research demonstrates evidence of significant cross-talk, even synergy, between OS and parasympathetic signaling in creating of a vulnerable AF substrate, experiments are conducted during development of embodiments herein to demonstrate that injection of NOX2 shRNA and $G\alpha_{i/o}$ inhibitory peptides—given either singly or in combination—reverse established AF substrate in a RAP model of AF.

NOX2 generated ROS is elevated in RAP atrium. Four dogs were subjected to RAP at 600 bpm for 3-4 weeks (no AV node ablation performed) (Ref. 13; herein incorporated by reference in its entirety). PLA from RAP dogs and 5 normal (control) dogs was assessed for $O^{2-}$ generation (Ref 14; herein incorporated by reference in its entirety) in the presence of different ROS inhibitors (for NOX2, mitochondrial ROS, xanthine oxidase and NOS). Total $O^{2-}$ was significantly elevated in RAP PLA, with NOX2 being a major contributor to total $O^{2-}$ (3 fold increase over normal;

p<0.05). The increase in NOX2 generated $O^{2-}$ was accompanied by >10 fold increase in gp91 (major NOX2 subunit) expression in RAP atrium compared to controls (p<0.01). Mitochondrial induced $O^{2-}$ was also elevated in RAP (1.5 fold increase over normal; p<0.05). NOX2 generated OS is significantly elevated in the setting of electrical remodeling in AF, indicating that it is a viable therapeutic target in AF.

AF leads to neural hypertrophy and parasympathetic/sympathetic nerve sprouting in the left atrium (Refs. 8, 15; herein incorporated by reference in their entireties). RAP model was created in 5 animals by RAP at 600 beats/min for 3-4 weeks (without AV node ablation). 5 normal dogs were used as controls. PLA and LAA sections were examined for parasympathetic and sympathetic nerves (acetylcholinesterase, dopamine β-hydroxylase). Nerve Growth Factor (NGF) expression assessed by PCR. The PLA displayed unique, large nerve bundles (>0.01 $mm^2$) in both RAP and control animals that were not seen in the LAA. In RAP compared to control: i) nerve bundles in the PLA were markedly larger and ii) parasympathetic nerve fibers predominated (FIG. 1). Sympathetic nerve fibers were also increased in RAP (4.8 vs 2.4 fibers/$mm^2$, p<0.05). Parasympathetic and sympathetic nerve growth correlated with increase in NGF expression in RAP GPs (>10 fold increase; p<0.01). RAP therefore induces marked neural hypertrophy and an increase in parasympathetic and sympathetic nerve fibers in the PLA.

Figure 2:
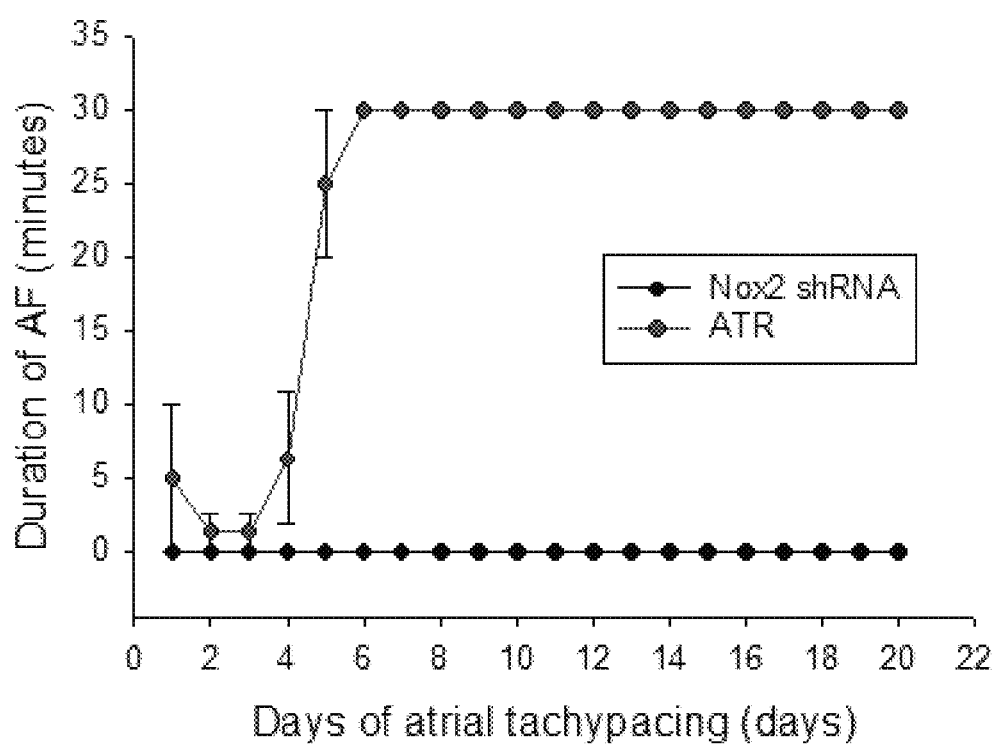
FIG. 2. Chronic expression of NOX2 shRNA prevents AF in RAP.
Figure 3:
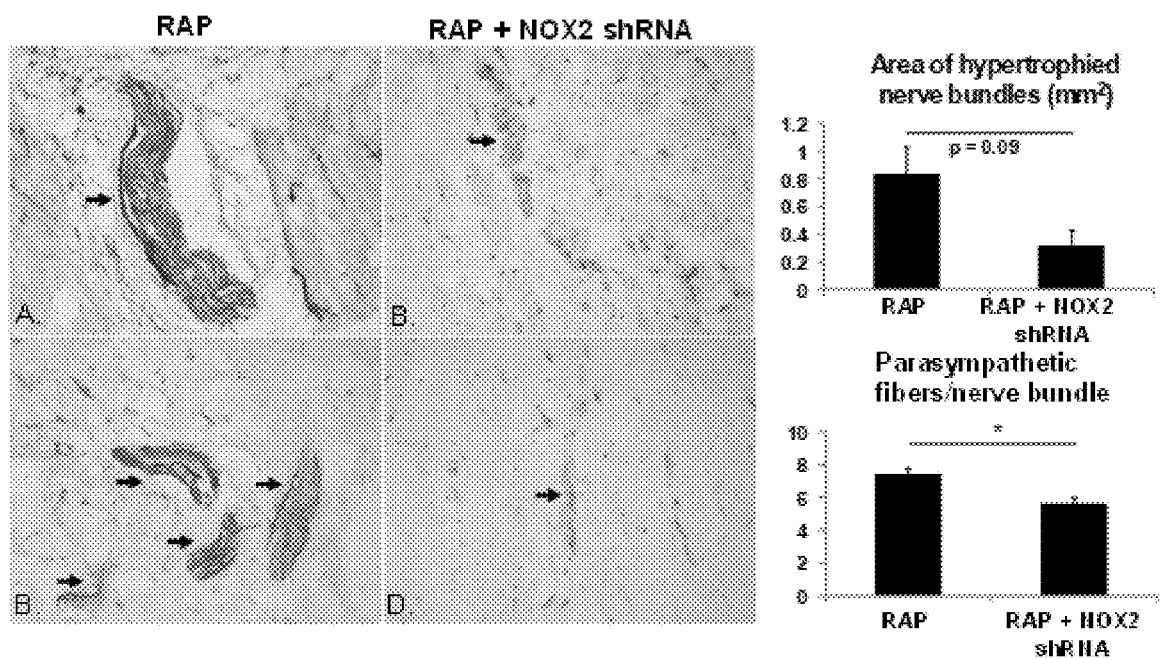
FIG. 3. NOX2 shRNA prevents neural hypertrophy and parasympathetic nerve sprouting in RAP.

NOX2 shRNA attenuates ERP shortening/AF and parasympathetic nerve sprouting in RAP atrium. Experiments were conducted during development of embodiments herein to demonstrate that NOX2 knockdown in PLA myocardium+GPs (4 weeks) will not only attenuate RAP induced ERP shortening, but will also attenuate RAP induced nerve growth/sprouting. In 3 animals, 10 mg of plasmid expressing NOX2 shRNA was injected sub-epicardially in the PLA, followed by electroporation to facilitate gene delivery. 7 control animals were also subjected to RAP (one injected with scrambled gene, one sham control, others subjected to RAP without a thoracotomy). One week after gene injection, the gene-injected animals were subjected to RAP at 600 bpm (without AV node ablation) for 20 days, followed by a terminal study. Every 48 hours, pacing was stopped in each animal for 30-60 minutes to assess for spontaneous AF (defined as AF that did not terminate during this period). Following a terminal study, NOX2 was measured (PCR, western blotting), NGF expression was assessed (PCR) and autonomic nerves were stained. FIG. 2 shows that the control dogs (scrambled gene and sham) developed sustained AF after 6 days of RAP. In contrast, no significant AF was noted in NOX2 shRNA animals (NOX2 shRNA vs controls, p<0.05; FIG. 2). ERPs were markedly longer in NOX2 shRNA dogs versus controls (124±25 vs<50 msec; p<0.05). NOX2 level was significantly decreased by NOX2 shRNA on PCR (50% decrease, p<0.05) and on western blotting. NGF was decreased in NOX2 shRNA injected PLA (~50% knockdown; p<0.05). Immunostaining showed that NOX2 shRNA injected PLA did not demonstrate the nerve bundle hypertrophy and parasympathetic hyperinnervation noted in RAP controls (FIG. 3). NOX2 shRNA prevents ERP shortening and AF in RAP. NOX2 inhibition also attenuates RAP induced parasympathetic nerve growth. OS induced parasympathetic growth is likely an important mechanism contributing to ERP shortening during RAP.

Even after 7 months of continuous RAP following gene injection, canine subject did not develop AF (only atrial flutter, which is to be expected with continuous RAP for such a long time). These data further validate NOX2 as a clinical target in AF.

Figure 4:
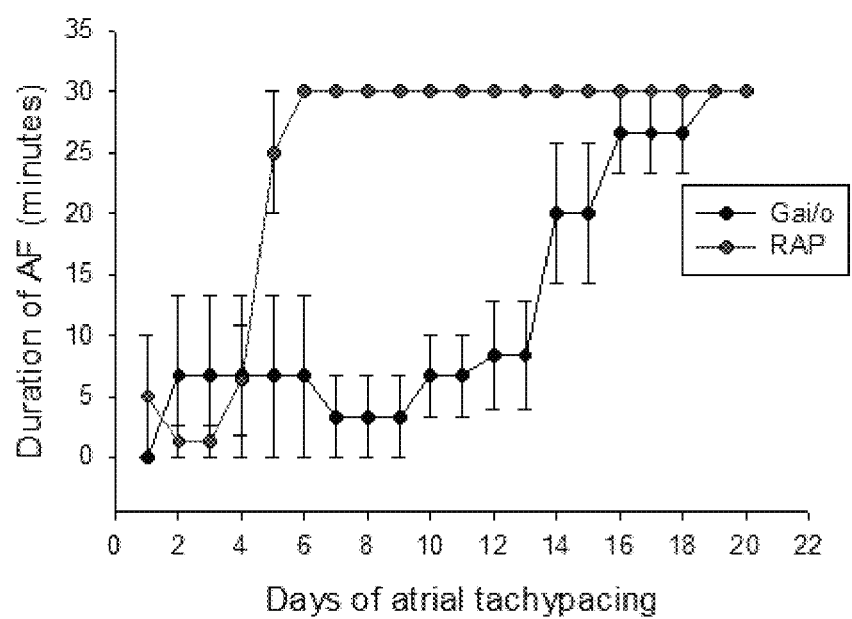
FIG. 4. G$\alpha$i/o minigene delays time to AF onset in RAP.

Minigene expressing $G\alpha_{i/o}$ inhibitory peptides ($G\alpha_{i/o}$-ct) attenuates ERP shortening and AF in RAP (Ref. 16; incorporated by reference in its entirety). In three animals, 10 mg of plasmid expressing $G\alpha_{i2}+G\alpha_{o1}$ peptide (under control of a long acting UBc promoter) was injected in the PLA. 5 control animals were also subjected to RAP (one injected with scrambled gene, one sham control, the other controls underwent RAP without a thoracotomy). All animals then underwent RAP at 600 bpm (without AV node ablation) for 20 days. Every 48 hours, pacing was stopped for 30-60 minutes to assess for sustained AF. FIG. 4 shows that $G\alpha_{i/o}$-ct results in a significant delay in AF onset in RAP dogs (p<0.05). This was accompanied by significant ERP prolongation (93±13 in $G\alpha_{i/o}$ vs<50 msec in controls; p<0.05). These data indicate that parasympathetic nerves contribute to ERP shortening and AF in RAP, and indicate that $G\alpha_{i/o}$ is has a beneficial effect on longer term electrical remodeling.

NOX2 shRNA+$G\alpha_{i/o}$ peptides is effective at preventing AF in RAP. A combination of NOX2 shRNA+minigene expressing $G\alpha_{i2}$+minigene expressing $G\alpha_{o1}$ in a canine subject. After 5 months of RAP, the canine has not developed sustained AF. Importantly, unlike the long term NOX2 shRNA dog which did develop sustained atrial flutter, this animal has shown only non-sustained flutter, with intervening episodes of sinus rhythm. These results indicate that synergy between NOX2 shRNA+$G\alpha_{i/o}$ peptides in preventing AF in RAP.

OS and parasympathetic signaling both contribute to electrical remodeling in RAP. Furthermore, OS inhibition markedly attenuates parasympathetic nerve growth/sprouting in RAP, indicating a close interplay between these mechanisms. In some embodiments, provided herein are methods and compositions for gene-based inhibition of OS and parasympathetic signaling—either singly or in combination—to reverse established electrical remodeling in a RAP model, with a resulting decrease in AF.

In some embodiments, compositions and methods for the inhibition of NOX2 are provided. Some exemplary methods and compositions for NOX2 inhibition are described, for example, in U.S. Pat. No. 9,932,588; incorporated by reference in its entirety. In some embodiments, the present invention provides methods of inhibiting a NOX2-mediated signaling event in a cell or tissue. These methods comprise administering to a cell or tissue, preferably a human cell or tissue, one of a modified NOX2 peptide and an isolated nucleic acid comprising a minigene which encodes a modified NOX2 peptide, whereby following the administration, the NOX2 peptide inhibits the NOX2-mediated signaling event in the cell or tissue.

In some embodiments, compositions and methods are provided for inhibiting NOX2 activity and/or expression.

In other embodiments, compositions and methods are provided for inhibiting the expression of NOX2. Multiple methods of altering gene expression within a cell, tissue, or subject are known in the field (e.g., RNAi, antisense RNA, gene therapy, CRISPR, etc.). In some embodiments, a nucleic acid is used to modulate expression of NOX2.

In some embodiments, the technology provides a method for inhibiting NOX2 activity by administering an antibody or fragment that recognizes, binds, and inhibits the activity of NOX2. In some embodiments, the antibody is a monoclonal antibody and in some embodiments the antibody is a polyclonal antibody. In some embodiments, the antibody is, for example, a human, humanized, or chimeric antibody.

In some embodiments, a NOX2 inhibitor comprises a small molecule. In some embodiments, the present invention provides a small molecule inhibitor of NOX2. In some embodiments, the present invention provides a small molecule drug or pharmaceutical compound configured to or capable of inhibiting NOX2 activity, function expression, or the like.

For example, in some embodiments a small interfering RNA (siRNA) is designed to target and degrade NOX2. siRNAs are double-stranded RNA molecules of 20-25 nucleotides in length. While not limited in their features, typically an siRNA is 21 nucleotides long and has 2-nt 3' overhangs on both ends. Each strand has a 5' phosphate group and a 3' hydroxyl group. In vivo, this structure is the result of processing by Dicer, an enzyme that converts either long dsRNAs or small hairpin RNAs (shRNAs) into siRNAs. However, siRNAs can also be synthesized and exogenously introduced into cells to bring about the specific knockdown of a gene of interest. Essentially any gene of which the sequence is known can be targeted based on sequence complementarity with an appropriately tailored siRNA. For example, those of ordinary skill in the art can synthesize an siRNA (see, e.g., Elbashir, et al., Nature 411: 494 (2001); Elbashir, et al. Genes Dev 15:188 (2001); Tuschl T, et al., Genes Dev 13:3191 (1999); incorporated by reference in their entireties).

In some embodiments, RNAi is utilized to inhibit expression of NOX2. In some embodiments, RNAi is used to modulate expression of NOX2. RNAi represents an evolutionarily conserved cellular defense for controlling the expression of foreign genes in most eukaryotes, including humans. RNAi is typically triggered by double-stranded RNA (dsRNA) and causes sequence-specific degradation of single-stranded target RNAs (e.g., an mRNA). The mediators of mRNA degradation are small interfering RNAs (siRNAs), which are normally produced from long dsRNA by enzymatic cleavage in the cell. siRNAs are generally approximately twenty-one nucleotides in length (e.g. 21-23 nucleotides in length) and have a base-paired structure characterized by two-nucleotide 3' overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, an RNase III enzyme (e.g., Dicer) converts the longer dsRNA into 21-23 nt double-stranded siRNA fragments. In some embodiments, RNAi oligonucleotides are designed to target the junction region of fusion proteins. Chemically synthesized siRNAs have become powerful reagents for genome-wide analysis of mammalian gene function in cultured somatic cells. Beyond their value for validation of gene function, siRNAs also hold great potential as gene-specific therapeutic agents (see, e.g., Tuschl and Borkhardt, Molecular Intervent. 2002; 2(3): 158-67, herein incorporated by reference).

In other embodiments, shRNA techniques (See e.g., U.S. Pub. No. 2008/0025958, herein incorporated by reference in its entirety) are utilized to modulate (e.g., inhibit) expression of NOX2. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it. shRNA is transcribed by RNA polymerase III.

In some embodiments, provided herein are small hairpin RNA (shRNA) directed against a NOX2 gene ("NOX2 shRNA"). The shRNA can be a unimolecular RNA that includes a sense sequence, a loop region, and an antisense sequence (sometimes referred to as first and second regions), which together form a hairpin loop structure. Preferably, the antisense and sense sequences are substantially complementary to one other (about 80% complementary or more), where in certain embodiments the antisense and sense sequences are 100% complementary to each other. In certain embodiments, the antisense and sense sequences are too short to be processed by Dicer, and hence act through an alternative pathway to that of longer double-stranded RNAs (e.g., shRNAs having antisense and sense sequences of about 16 to about 22 nucleotides in length, e.g., between 18 and 19 nucleotides in length (e.g., an sshRNA). Additionally, the antisense and sense sequences within a unimolecular RNA of the invention can be the same length, or differ in length by less than about 9 bases. The loop can be any length, with the preferred length being from 0 to 4 nucleotides in length or an equivalent length of non-nucleotidic linker, and more preferably 2 nucleotides or an equivalent length of non-nucleotidic linker (e.g., a non-nucleotide loop having a length equivalent to 2 nucleotides). In one embodiment, the loop is: 5'-UU-3' (rUrU) or 5'-tt-3', where "t" represents deoxythymidine (dTdT). Within any shRNA hairpin, a plurality of the nucleotides are ribonucleotides. In the case of a loop of zero nucleotides, the antisense sequence is linked directly to the sense sequence, with part of one or both strands forming the loop. In a preferred embodiment of a zero-nt loop shRNA, the antisense sequence is about 18 or 19 nt and the sense sequence is shorter than the antisense sequence, so that one end of the antisense sequence forms the loop.

A hairpin of representative shRNA's can be organized in either a left-handed (L) hairpin (i.e., 5'-antisense-loop-sense-3') or a right-handed (R) hairpin (i.e., 5'-sense-loop-antisense-3'). Furthermore, an shRNA may also contain overhangs at either the 5' or 3' end of either the sense sequence or the antisense sequence, depending upon the organization of the hairpin. Preferably, if there are any overhangs, they are on the 3' end of the hairpin and comprise between 1 to 6 bases. The presence of an overhang is preferred for R-type hairpins, in which case a 2-nt overhang is preferred, and a UU or tt overhang is most preferred.

Modifications can be added to enhance shRNA stability, functionality, and/or specificity and to minimize immunostimulatory properties. For example, the overhangs can be unmodified, or can contain one or more specificity or stabilizing modifications, such as a halogen or O-alkyl modification of the 2' position, or internucleotide modifications such as phosphorothioate modification. The overhangs can be ribonucleic acid, deoxyribonucleic acid, or a combination of ribonucleic acid and deoxyribonucleic acid.

In another non-limiting example of modifications that can be applied to left handed hairpins, 2'-O-methyl modifications (or other 2' modifications, including but not limited to other 2'-O-alkyl modifications) can be added to nucleotides at position 15, 17, or 19 from the 5' antisense terminus of the hairpin, or any two of those positions, or all three, as well as to the loop nucleotides and to every other nucleotide of the sense sequence except for nucleotides 9, 10 and 11 from the 5'-most nucleotide of the sense sequence (also called the 9.sup.th, 10.sup.th, and 11.sup.th nucleotides), which should have no modifications that block "slicing" activity. Any single modification or group of modifications described in the preceding sentence can be used alone or in combination with any other modification or group of modifications cited.

Ui-Tei, K. et al. (*Nucl. Acids Res.* (2008) 36 (22): 7100-7109) observed that the specificity of siRNAs can be increased by modifying the seed region of one or both strands. Such modifications are applicable to shRNA's of the present disclosure. In another non-limiting example of modifications that can be applied to hairpins, nt 1-6 of the antisense sequence and nt 14-19 of the sense sequence can be 2'-O-methylated to reduce off-target effects. In a preferred embodiment, only nt 1-6 are modified from 2'-OH to 2'-H or 2'-O-alky.

As the sense sequence of an shRNA can potentially enter RISC and compete with the antisense (targeting) strand, modifications that prevent sense sequence phosphorylation are valuable in minimizing off-target signatures. Thus, desirable chemical modifications that prevent phosphorylation of the 5' carbon of the 5'-most nucleotide of right-handed shRNA of the invention can include, but are not limited to, modifications that: (1) add a blocking group (e.g., a 5'-O-alkyl) to the 5' carbon; or (2) remove the 5'-hydroxyl group (e.g., 5'-deoxy nucleotides) (see, e.g., WO 2005/078094).

In addition to modifications that enhance specificity, modifications that enhance stability can also be added. In one embodiment, modifications comprising 2'-O-alkyl groups (or other 2' modifications) can be added to one or more, and preferably all, pyrimidines (e.g., C and/or U nucleotides) of the sense sequence. Modifications such as 2' F or 2'-O-alkyl of some or all of the Cs and Us of the sense sequence/region, respectively, or the loop structure, can enhance the stability of the shRNA molecules without appreciably altering target specific silencing. It should be noted that while these modifications enhance stability, it may be desirable to avoid the addition of these modification patterns to key positions in the hairpin in order to avoid disruption of RNAi (e.g., that interfere with "slicing" activity).

Additional stabilization modifications to the phosphate backbone may be included in the shRNAs in some embodiments of the present invention. For example, at least one phosphorothioate, phosphordithioate, and/or methylphosphonate may be substituted for the phosphate group at some or all 3' positions of nucleotides in the shRNA backbone, or any particular subset of nucleotides (e.g., any or all pyrimidines in the sense sequence of the oligonucleotide backbone), as well as in any overhangs, and/or loop structures present. These modifications may be used independently or in combination with the other modifications disclosed herein.

Description of modified shRNAs of interest can be found in the following references, both of which are incorporated herein by reference in their entirety: Q. Ge, H. Ilves, A. Dallas, P. Kumar, J. Shorenstein, S. A. Kazakov, and B. H. Johnston (2010) Minimal-length short hairpin RNAs: The Relationship of Structure and RNAi Activity. RNA 16(1): 106-17 (Epub Dec. 1, 2009); and Q. Ge, A. Dallas, H. Ilves, J. Shorenstein, M. A. Behlke, and B. H. Johnston (2010) Effects of Chemical Modification on the Potency, Serum Stability, and Immunostimulatory Properties of Short shRNAs. RNA 16(1):118-30 (Epub Nov. 30, 2009).

Modified shRNAs according to aspects of the present invention may include additional chemical modifications for any of a variety of purposes, including 3' cap structures (e.g., an inverted deoxythymidine), detectable labels conjugated to one or more positions in the shRNA (e.g., fluorescent labels, mass labels, radioactive labels, etc.), or other conjugates that can enhance delivery, detection, function, specificity, or stability (e.g., amino acids, peptides, proteins, sugars, carbohydrates, lipids, polymers, nucleotides, polynucleotides, etc.). Combinations of additional chemical modifications may be employed as desired by the user.

Suitable NOX2 shRNAs include those nucleic acids ranging from about 20 nucleotides to about 80 nucleotides in length, wherein a portion of the nucleic acids have a double-stranded structural domain ranging from about 15 nucleotides to about 25 nucleotides in length. In some aspects, the shRNA can include modified bases or phosphodiester backbones to impart stability of the shRNA inside tissues and cells. An exemplary NOX2 shRNA includes SEQ ID NO: 34 (5'→3' Nucleotide Sequence: CCGCC-TATGACTTGGAAATGGATACTCGAGTATCCATTTC-CAAGTCATAG GTTTTTG). In some embodiments, an exemplary NOX2 shRNA (or other inhibitory nucleic acid) is one that targets the sequence of SEQ ID NO: 1.

In some embodiments, an antisense nucleic acid (e.g., an antisense DNA oligo, an antisense RNA oligo) is used to modulate the expression of NOX2. For example, in some embodiments, expression of NOX2 is inhibited using antisense compounds that specifically hybridize with nucleic acids NOX2. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation (e.g., inhibition) of the expression of NOX2.

In some embodiments, NOX2 activity and/or expression are inhibited using the CRISPR/Cas system. "CRISPRs" (clustered regularly interspaced short palindromic repeats), as described herein, are segments of prokaryotic DNA containing short repetitions of base sequences. Each repetition is followed by short segments of "spacer DNA" from previous exposures to a bacterial virus or plasmid. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. CRISPR/Cas system has been used for gene editing (adding, disrupting or changing the sequence of specific genes) and gene regulation in species throughout the tree of life. By delivering the Cas9 protein and appropriate guide RNAs into a cell, the organism's genome can be cut at any desired location. One can use CRISPR to build RNA-guided gene editing tools capable of altering the genome of a subject. In some embodiments, the CRISPR/Cas system is utilized to inhibit (e.g., partially or completely) the expression of NOX2 in a subject, tissue, or cells. In some embodiments, the CRISPR/Cas system is utilized to produce NOX2 that is of reduced activity (e.g., in a subject, tissue, or cells.

In some embodiments, agents that disrupt autonomic pathways (e.g., pathways involved in AF) are provided. In some embodiments, the present invention provides compositions and methods which disrupt (e.g. block, inhibit, etc.) autonomic pathways. In some embodiments, the present invention provides G-protein inhibitors which disrupt autonomic pathways. In some embodiments, delivery of G-protein inhibitors that selectively block sympathetic or parasympathetic pathways are provided. In some embodiments, provided herein are compositions and methods for the treatment and prevention of atrial fibrillation that block G protein coupled receptor mediated signaling. In some embodiments, the present invention provides compositions and methods that employ G-protein inhibitors that disrupt autonomic pathways in the heart as a treatment for atrial fibrillation. In some embodiments, the present invention provides G-protein inhibitors to treat a condition or disorder of the heart (e.g. atrial fibrillation). In some embodiments, the present invention provides an inhibitor of G-protein function.

In some embodiments, a G-protein inhibitor is a G-protein inhibitory peptide. In some embodiments, the present invention provides peptides of any suitable amino acid sequence capable of inhibiting one or more G-proteins. In some embodiments, peptides provided by or encoded by the compositions of embodiments of the present invention may comprise any arrangement of any standard amino acids (e.g. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) or non-standard amino acids (e.g. D-amino acids, chemically or biologically produced derivatives of common amino acids, selenocysteine, pyrrolysine, lanthionine, 2-aminoisobutyric acid, dehydroalanine, etc.). In some embodiments, G-protein inhibitory peptides are inhibitors to Gα (e.g. GαI, Gαs, Gαq, Gα11, Gα12, Gα13, Gα14, G15, Gαo1, Gα16, etc.), GαI, and/or Gαs. In some embodiments, these peptide sequences mimic the C-terminus of Gα (e.g., Gαo1), GαI, and/or Gαs so as to block receptor/G protein interactions (e.g. 5 C-terminal amino acids, 6 C-terminal amino acids, 7 C-terminal amino acids, 8 C-terminal amino acids, 9 C-terminal amino acids, 10 C-terminal amino acids, 11 C-terminal amino acids, 12 C-terminal amino acids, 13 C-terminal amino acids, 14 C-terminal amino acids, 15 C-terminal amino acids, 16 C-terminal amino acids, 17 C-terminal amino acids, 18 C-terminal amino acids, 19 C-terminal amino acids, 20 C-terminal amino acids, 30 C-terminal amino acids, 40 C-terminal amino acids, 50 C-terminal amino acids, full C-terminal region, etc.).

In some embodiments, for example, a G-protein inhibitory peptide of the present invention comprises the C-terminus of Gαi (NCBI Accession Number ACN58588.1; GI:224586986). In some embodiments, for example, a G-protein inhibitory peptide of the present invention comprises the 11 C-terminal amino acids of Gαi (e.g. amino acid sequence IKNNLKDCGLF (SEQ ID NO:3)). In some embodiments, a G-protein inhibitory peptide comprises at least 50% (e.g., 50%, 55%, 60%, 65%, 70%, 75%, 80%, 85%, 90%, 95%, 100%, or ranges therebetween) sequence identity with SEQ ID NO: 3.

In certain embodiments, a G-protein inhibitory peptide of the present invention comprises the C-terminus of Gαo1 (see, full sequences at NCBI Accession Number AAH30027; nucleic acid sequence NM-020988). In some embodiments, for example, a G-protein inhibitory peptide of the present invention comprises the 11 C-terminal amino acids of Gαi (e.g. amino acid sequence IANNLRGCGLY (SEQ ID NO:4)). In some embodiments, a G-protein inhibitory peptide comprises at least 50% (e.g., 50%, 55%, 60%, 65%, 70%, 75%, 80%, 85%, 90%, 95%, 100%, or ranges therebetween) sequence identity with SEQ ID NO: 4.

In some embodiments, peptides are provided that mimic the C-terminus of Gα (e.g. GαI, Gαs, Gαq, Gα11, Gα12, Gα13, Gα14, Gα15, Gαo1, Gα16, etc.), GαI, and/or Gαs to competitively inhibit G-protein interactions. In some embodiments, G-protein inhibitory peptides are fragments of a G-protein. In some embodiments, G-protein inhibitory peptides mimic the C-terminus of a G-protein (e.g. GαI, Gαs, Gα, Gαo1, etc.), but vary from the wild-type sequence (e.g. different length, variant amino acids, etc.). In some embodiments, peptides are variant forms of G-proteins or fragments thereof. In some embodiments, peptides provided are variant sequences of the C-terminus of GαI, Gαs, and/or Gα (e.g. GαI, Gαs, Gαq, Gα11, Gα12, Gα13, Gα14, Gα15, Gαo1, Gα16, etc.). In some embodiments, G-protein inhibitory peptides are provided to a subject as isolated or purified peptides. In some embodiments, G-protein inhibitory peptides are provided to a subject as nucleic acid molecules that encode such peptides. In some embodiments, peptides are optimized to enhance cell penetration (e.g. sequence optimization, sequence tag, tagged with a small molecule, etc.).

In some embodiments, compositions and method comprise a Gα$_i$ and/or Gα$_o$ inhibitory peptide or nucleic acid encoding a Gα$_i$ and/or Gα$_o$ inhibitory peptide. The components of an nucleic acid encoding a Gα$_i$ and/or Gα$_o$ inhibitory peptide will vary and will include, at a minimum, a vector that contains a nucleic acid sequence encoding a Gα$_i$ and/or Gα$_o$ inhibitory peptide and the necessary components for expression of the Gα$_i$ and/or Gα$_o$ inhibitory peptide from the vector. Nucleic acid sequence encoding for any Gα$_i$ and/or Gα$_o$ inhibitory peptide may find use herein.

In some embodiments, a minigene encoding a Gα$_i$ and/or Gα$_o$ inhibitory peptide is provided in a pharmaceutic composition and/or administered to a subject. As used herein the term "minigene" refers to a minimal gene fragment that excludes one or more components of a native gene locus but includes the necessary elements for expression of the gene product or some portion of the gene product or a synthetic construct. In some instances, Gα$_i$ and/or Gα$_o$ inhibitory peptide minigene may exclude at least one intron, or portion thereof. In some instances, a minigene may include at least one intron, or portion thereof. In some embodiments, a minigene will include at least some regulatory sequence that controls or enhances the expression of the minigene transcript. In some instances, a minigene regulatory sequence will include a promoter. Promoters useful in a minigene will vary and selection of such a minigene promoter will depend on various factors including the desired expression level of the minigene transcript, the desired control of minigene expression, the desired size of the overall minigene, the intended use of the minigene, including the subject to which the minigene may be delivered. Such minigene promoters may include but are not limited to a native promoter, a non-native, a heterologous promoter, a minimal promoter, a minipromter, a constitutive promoter, a tissue specific promoter, an inducible promoter, a synthetic promoter, and the like.

In some embodiments, the nucleotide sequence of a minigene of the invention is one of SEQ ID NOs: 20, 21, 22, 23, 24, 25, 26, 27, 28, 29, 30, 31, 32, and 33 (FIG. 10). In some embodiments, the nucleotide sequence of a minigene of the invention comprises at least 50% (e.g., 50%, 55%, 60%, 65%, 70%, 75%, 80%, 85%, 90%, 95%, 100%, or ranges therebetween) sequence identity with one of SEQ ID NOs: 20, 21, 22, 23, 24, 25, 26, 27, 28, 29, 30, 31, 32, and 33. In some embodiments, a minigene sequence is provided in a vector for delivery to a subject (e.g., a plasmid, a viral vector, etc.).

In some instances, a nucleic acid encoding a $G\alpha_i$ and/or $G\alpha_o$ inhibitory peptide will include a vector backbone, e.g., a plasmid polynucleotide backbone. Vector backbones useful in embodiments herein will vary and may be selected based on a number of factors. A vector may include one or more vector specific elements. By "vector specific elements" is meant elements that are used in making, constructing, propagating, maintaining and/or assaying the vector before, during or after its construction and/or before its use. Such vector specific elements include but are not limited to, e.g., vector elements necessary for the propagation, cloning and selection of the vector during its use and may include but are not limited to, e.g., an origin of replication, a multiple cloning site, a prokaryotic promoter, a phage promoter, a selectable marker (e.g., an antibiotic resistance gene, an encoded enzymatic protein, an encoded fluorescent or chromogenic protein, etc.), and the like. Any convenient vector specific elements may find use, as appropriate, in the vectors as described herein.

In some embodiments, a G-protein inhibitor is provided from an isolated nucleic acid comprising a minigene, wherein said minigene encodes a modified carboxy terminal $G\alpha$ peptide, wherein the peptide blocks the site of interaction between a G protein and a G protein coupled receptor in a cell, such as a human cell. In addition, the minigene can further comprise one or more of a promoter, a ribosomal binding site, a translation initiation codon, and a translation termination codon. In some embodiments, the minigene encodes a modified carboxy terminal $G\alpha$ peptide (e.g., $G\alpha o1$ peptide) having one of the following general formulas: MGX, MX, and MZX, wherein M is a methionine amino acid residue, wherein G is a glycine amino acid residue, wherein Z is an amino acid residue other than a glycine amino acid residue, and wherein X is a carboxy terminal $G\alpha$ peptide which comprises an amino acid sequence of the carboxy terminus of a $G\alpha$ subunit, and has the property of binding a G protein coupled receptor. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a $G\alpha$ subunit. For example, the amino acid sequence of a modified carboxy terminal $G\alpha$ peptide is one of SEQ ID NOs: 5, 6, 7, 8, 9, 10, 11, 12, 13, 14, 15, 16, 17, 18, and 19 (FIG. 9). In some embodiments, the amino acid sequence of a modified carboxy terminal $G\alpha$ peptide comprises at least 50% (e.g., 50%, 55%, 60%, 65%, 70%, 75%, 80%, 85%, 90%, 95%, 100%, or ranges therebetween) sequence identity with one of SEQ ID NOs: 5, 6, 7, 8, 9, 10, 11, 12, 13, 14, 15, 16, 17, 18, and 19.

Exemplary inhibitors of the present invention include those described in U.S. Pat. Publ. 20030162258, 20070231830, and 20070077597, each of which is herein incorporated by reference in its entirety. These references further describe methods for identifying and selecting additional inhibitors. Other G-protein inhibitors, such as small molecules, RNAi, siRNA, shRNA, antisense compounds, genetic manipulation, antibodies, etc. are described, for example, in U.S. Pat. Nos. 8,518,884; 8,193,151; and 6,559,128; each of which is incorporated by reference in their entireties.

In some embodiments, methods herein comprise treating patients with AF undergoing open heart surgery. Post-operative AF occurs in over one third of patients undergoing cardiac surgery and significantly contributes to procedure-related morbidity. In addition to open-heart surgery, an increasing number of surgeons are performing ablation (PVI) via a minimally invasive epicardial approach. To treat existing AF or to prevent post-op AF, the transgene(s) described herein are injected in the atria during any of these epicardial procedures.

In some embodiments, a subject administered the compositions and/or methods herein suffers from a heart condition, such as atrial fibrillation or the other conditions discussed herein. In such embodiments, compositions and methods herein are utilized to treat such a condition. In some embodiments, a subject administered the compositions and/or methods herein is at risk (e.g., possesses risk factors for) a heart condition, such as atrial fibrillation or the other conditions discussed herein. In such embodiments, compositions and methods herein are utilized to prevent such a condition.

In some embodiments, uptake, expression, and or delivery of any agents administered in embodiments herein may be enhanced by the delivery techniques, devices, and/or methods described in, for example U.S. Pat. Nos. 6,559,128; 8,193,151; 8,518,884; 9,078,918; 9,932,588; 10,369,360; U.S. Prov. App. No. 62/961,514; herein incorporated by reference in their entireties. For example, some embodiments comprise electroporation of tissue to enhance delivery.

Various embodiments herein are described for the treatment of atrial fibrillation or cardiac arrhythmias. However, the compositions and methods described herein (e.g., for the treatment of atrial fibrillation or cardiac arrhythmias) may also find use in the treatment or prevention of other conditions and/or diseases of the heart. In some embodiments, the present invention provides treatment or prevention of a heart disease or condition selected from the list of aortic dissection, cardiac arrhythmia (e.g. atrial cardiac arrhythmia (e.g. premature atrial contractions, wandering atrial pacemaker, multifocal atrial tachycardia, atrial flutter, atrial fibrillation, etc.), junctional arrhythmias (e.g. supraventricular tachycardia, AV nodal reentrant tachycardia, paroxysmal supraventricular tachycardia, junctional rhythm, junctional tachycardia, premature junctional complex, etc.), atrio-ventricular arrhythmias, ventricular arrhythmias (e.g. premature ventricular contractions, accelerated idioventricular rhythm, monomorphic ventricular tachycardia, polymorphic ventricular tachycardia, ventricular fibrillation, etc.), etc.), congenital heart disease, myocardial infarction, dilated cardiomyopathy, hypertrophic cardiomyopathy, aortic regurgitation, aortic stenosis, mitral regurgitation, mitral stenosis, Ellis-van Creveld syndrome, familial hypertrophic cardiomyopathy, Holt-Orams Syndrome, Marfan Syndrome, Ward-Romano Syndrome, and/or similar diseases and conditions.

EXPERIMENTAL

Example 1

Reversing Electrical Remodeling in Dogs Subjected to Rapid Atrial Pacing (RAP) by NOX2 shRNA If OS leads to creation/maintenance of electrical remodeling in AF, inhibition of NOX2 will at reverse ERP shortening in dogs with established electrical remodeling.

Dogs undergo RAP for 3 weeks, followed by cardioversion to sinus rhythm and injection of NOX2 shRNA. The dogs are allowed to stay in sinus rhythm for one week, to allow time for gene expression. RAP will then be resumed, and time to AF recurrence determined.

Since neither antiarrhythmic drugs nor ablation are very effective at achieving acute cardioversion of AF, their efficacy is typically measured by time to recurrence of AF (after a patient is cardioverted or ablated to sinus rhythm) (Refs. 25, 35, 36; herein incorporated by reference in their entireties). Trans-gene efficacy is examined by assessing time to onset (or recurrence) of AF in the canine model.

Preparation of Trans-Genes:

A plasmid under the control of the polymerase III promoter—U6—is used to express NOX2 shRNA or scrambled shRNA. Several weeks of gene expression has been obtained with this promoter.

Creation of RAP Model of AF:

An atrial pacemaker is implanted via jugular venous approach (ref 8; herein incorporated by reference in its entirety). One week later, RAP is initiated at 600 beats/min×3 weeks.

Open-Chest Electrophysiological Mapping:

After 3 weeks of RAP, the dogs are cardioverted to sinus rhythm. Open-chest mapping is performed. Effective refractory periods (ERPs) and atrial conduction is assessed (Refs. 8, 10, 37; herein incorporated by reference in their entireties).

Injection of Gene:

After baseline mapping, either NOX2 shRNA or scrambled shRNA is injected in both atria.

Gene Injection Protocol:

Plasmid is diluted in 8 ml saline and injected sub-epicardially (4 ml each atrium). As previously described (Refs. 11-12; herein incorporated by reference in their entireties), 4-6 injections reliably cover an entire atrium (0.5-1 ml per injection). Left atrial injection includes the PVs, PLA, right atrial injection the SVC/RA junction, RA free wall. After gene injection, electroporation is performed using Genetrodes (Harvard Apparatus) as previously reported by us (Refs. 11-12, 38; herein incorporated by reference in their entireties).

Re-Initiation of RAP:

After 1 week in sinus rhythm, RAP is re-initiated and continued for 6 months (26 weeks) or until the onset of AF. The time to the re-induction of sustained AF is monitored in all dogs. Every 48 hours, pacing is stopped for 30-60 minutes to assess for sustained AF. Sustained AF will be defined as AF that does not terminate during this period.

Open-Chest Mapping.

Once AF has begun to sustain, the dog is cardioverted to sinus rhythm and a terminal, open-chest study performed. ERPs, conduction is determined as at baseline (Refs. 8-9; herein incorporated by reference in its entirety).

Data Analysis:

Electrophysiological Analysis:

All electrophysiological variables (e.g. ERPs, conduction inhomogeneity index, AF duration etc) are compared between the different groups. Each active gene is compared with its respective control, using Bonferroni corrected t-tests. The three active gene groups are compared with each other using ANOVA (followed by Bonferroni corrected post-hoc t-tests) to determine which with gene group is most effective at reversing electrical remodeling in AF. Effect sizes are calculated separately for males and females to obtain an estimate of gender differences.

Homogeneity of gene expression is assessed in dogs receiving FLAG expressing plasmid by assessing immunofluorescence in atrial sections taken from gene injected regions of the atrium.

NOX2 Knockdown by shRNA:

% NOX2 knockdown is assessed by RT-PCR, western blotting.

Attenuation of Oxidative Damage:

Protein carbonyls is quantified by a DNPH-based immunoassay (Ref 39; herein incorporated by reference in its entirety). $O^{2-}$ generation is assessed by lucigenin chemiluminescence (Ref. 14; herein incorporated by reference in its entirety). Using appropriate substrates, both NOX2 and mitochondrial generated $O^{2-}$ are determined.

Inflammation:

An open chest approach and/or CpG motifs in naked DNA may cause atrial inflammation (Refs. 40-41; herein incorporated by reference in their entireties). Atrial inflammation is assessed (e.g., neurophil/macrophage infiltration, apoptosis, etc).

Fibrosis:

Masson Trichrome staining is performed and fibrosis quantified.

Signaling Pathways:

ROS activated signaling pathways is measured (e.g. CAMKII, PKC, etc.).

Example 2

Targeted Inhibition of Parasympathetic Signaling—with Minigene Expressing C-Terminal $G\alpha_{i/o}$ Inhibitory Peptides ($G\alpha_{i/o}$-Ct)—Reverses Electrical Remodeling in RAP If parasympathetic signaling causes electrical remodeling, $G\alpha_{i/o}$-ct will reverse ERP shortening and prevent/delay AF re-induction in RAP.

Dogs undergo RAP for 3 weeks, followed by cardioversion to sinus rhythm and injection of transgene ($G\alpha_{i/o}$-ct. The dogs are allowed to stay in sinus rhythm for one week, to allow time for gene expression. RAP is then be resumed and continued for 6 months (26 weeks) or until the onset of AF. At a terminal study, ERPs are determined. Dogs are injected with minigene expressing $G\alpha_{i/o}$-ct (see table 1). A plasmid under the control of long acting human polyubiquitin C (UBc) promoter is used to express $G\alpha_{i/o}$-ct. This plasmid also has a FLAG tag, which is used as a marker gene to assess homogeneity of gene expression. Sympathetic and parasympathetic nerves are stained (Refs. 37, 42; herein incorporated by reference in its entirety) and expression/activity of autonomic signaling proteins (e.g., PKA, cAMP, etc.) is assessed.

TABLE 1

| Aim 1: | |
|---|---|
| NOX2 shRNA | N = 7 dogs |
| Scrambled shRNA | N = 5 dogs |
| Aim 2: | |
| $G\alpha_{i/o}$ | N = 7 dogs |
| NOX2 shRNA + $G\alpha_{i/o}$ | N = 7 dogs |
| $G_R$ (scrambled) | N = 5 dogs |

Example 3

NOX2 shRNA and $G\alpha_{i/o}$-Ct when Given in Combination are at Reversing Electrical Remodeling in RAP OS and parasympathetic signaling act synergistically in creating AF, NOX2 shRNA+$G\alpha_{i/o}$-ct more effectively reverse ERP shortening than either gene alone. In some embodiments, combination of $G\alpha_{i/o}$-ct and NOX2 shRNA is more effective at attenuating ERP shortening and thus decreasing AF than either gene alone.

Example 4

Figure 5:
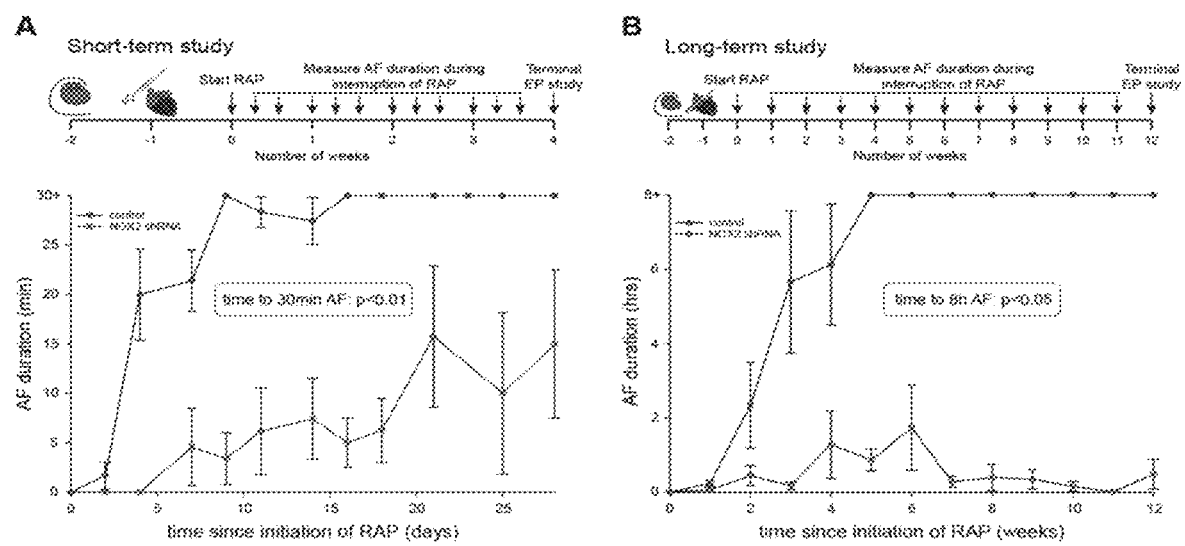
FIG. 5. NOX2 shRNA prevents development of sustained AF. (A) For our short-term study, animals who received NOX2 shRNA developed significantly shorter AF, with a delay in development of sustained AF>30 minutes. N=3-12 for controls, n=3-5 for NOX2 shRNA. (B) For our long-term study, NOX2 shRNA gene injection prevented development of sustained AF>8 hours. For A and B, n=3-12 for controls, n=3-7 for NOX2 shRNA. Data are mean±SEM. Significance by log-rank test indicated in graph.

NOX2 shRNA Attenuates Electrical Remodeling and Parasympathetic Nerve Sprouting in RAP Dogs NOX2 shRNA prevents ERP shortening/AF in RAP—Seven dogs underwent sub-epicardial injection of NOX2 shRNA in the atria, followed by electroporation to facilitate myocardial gene transfer. The gene injection and electroporation procedure were limited to the PLA in the first 4 animals, with subsequent three animals receiving gene injection in the left atrial free wall, LAA, and right atrium as well. Eighteen animals receiving either injection of scrambled shRNA or no gene injection were used as control. FIGS. 5A and 5B show detail of the experimental design for assessment of AF both in the short term (i.e. 4 weeks of RAP) and in the long term (i.e. 12 weeks of RAP). After gene injection, animals were subjected to RAP and duration of induced AF was subsequently recorded during periods in which RAP was interrupted. FIG. 5A shows the duration of AF after initiation of RAP: whereas control animals developed sustained AF for more than 30 minutes within a median of 4 days of RAP (interquartile range (IQR) 4-9 days), it took a median of 21 days for NOX2 shRNA animals to develop this AF burden (p<0.01). Three animals in each group were followed for twelve weeks to assess development of persistent AF (defined as AF duration>8 hours). FIG. 5B shows that it took a median of 14 days for control animals to develop >8 hours of AF. In contrast, it took NOX2 shRNA animals a median of 28 days to develop AF>8 hours (p<0.05). Over the entire recorded period, control animals spent a median of 60 minutes in AF (IQR 30-60 minutes), whereas NOX2 shRNA animals spent a median of 0 minutes in AF (IQR 0-2 minutes) (p=0.003). ERPs were markedly longer in NOX2 shRNA dogs versus controls (97±52 vs 46±20 msec; p<0.05). Following a terminal study, NOX2 was measured (PCR, western blotting), NGF expression was assessed (PCR) and autonomic nerves were stained. NOX2 level was significantly decreased by NOX2 shRNA on PCR (50% decrease, p<0.05) and on western blotting. NGF was decreased in NOX2 shRNA injected PLA (~50% knockdown; p<0.05). Immunostaining showed that NOX2 shRNA injected PLA did not demonstrate the nerve bundle hypertrophy and parasympathetic hyper-innervation noted in RAP controls (FIG. 3). It was also discovered that of the major ion channels that contribute to ERP shortening in AF—$I_{CaL}$, $I_{KI}$ and constitutively active $I_{KAch}$ (called $I_{KH}$), the amplitude of $I_{KH}$ was significantly reduced in NOX2 shRNA injected atria (data not shown due to space constraints). Conclusions: NOX2 shRNA prevents RAP induced ERP shortening, AF and parasympathetic nerve growth. Experiments indicate that oxidative injury induced parasympathetic growth contributes to ERP shortening in AF. Two of the NOX2 shRNA injected dogs were followed for 8 months after gene injection. These dogs did not develop AF during the entire follow up period. The explanted atria continued to show significant NOX2 downregulation.

Example 5

NOX2 shRNA Prevents Atrial Fibrosis in HF Model

Figure 6:
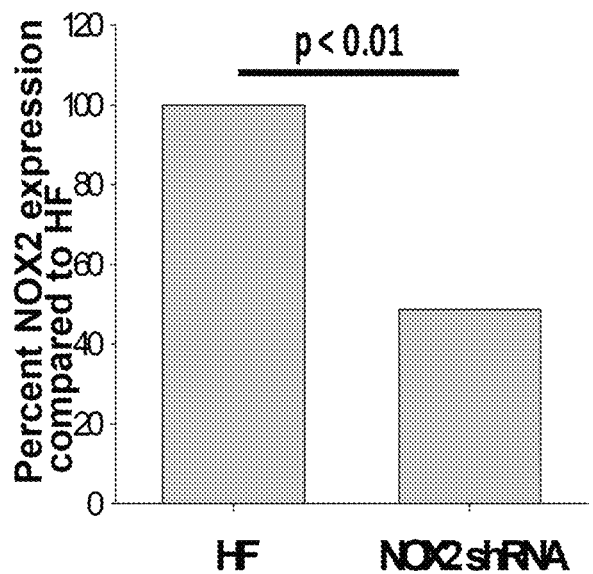
FIG. 6. Decrease in NOX2 expression in atria transfected with NOX2 shRNA.
Figure 6:
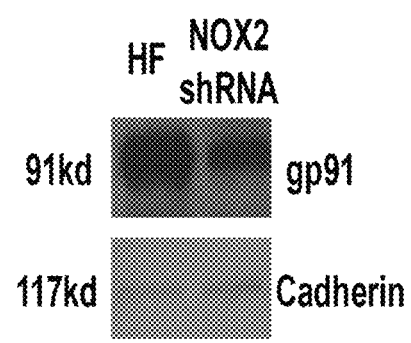
Figure 7:
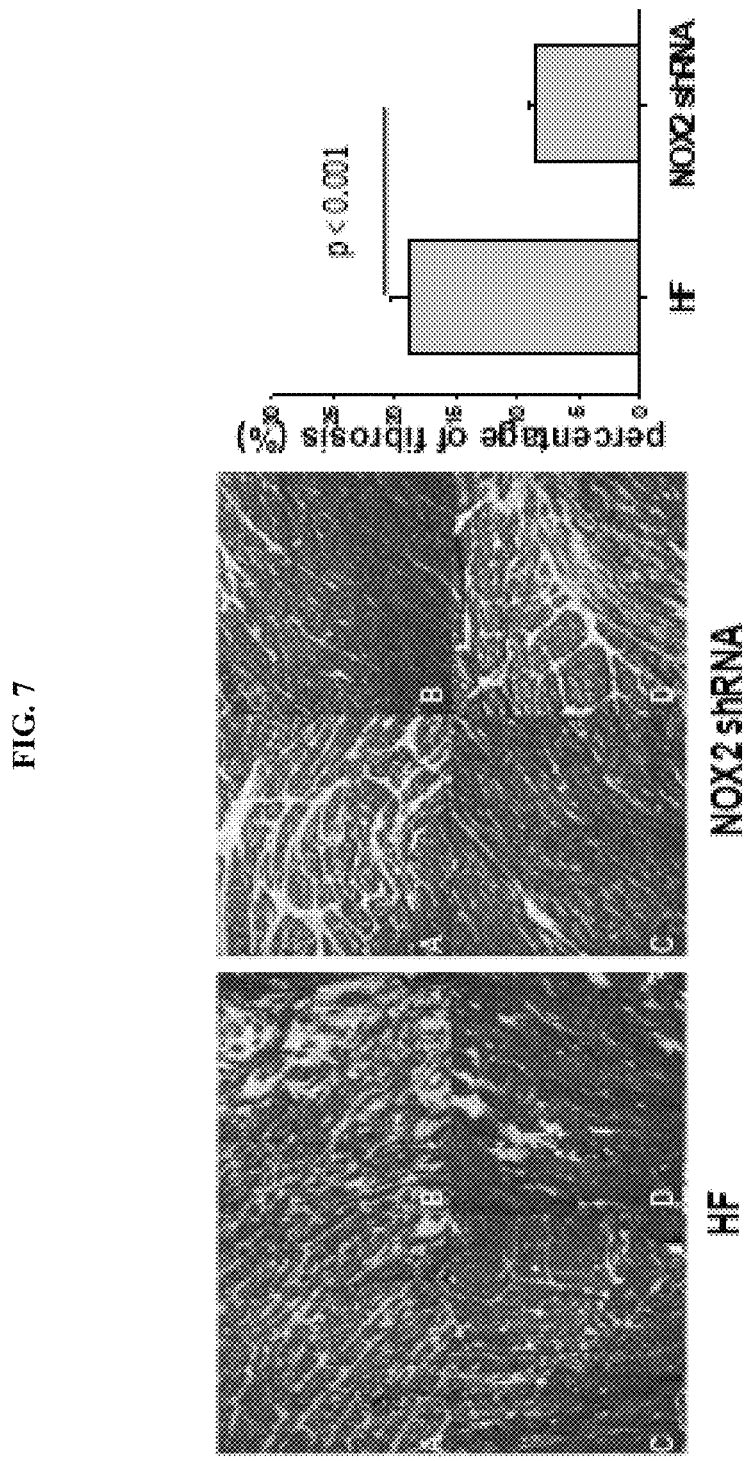
FIG. 7. Decrease in atrial fibrosis with NOX2 shRNA

NOX2-generated oxidative injury plays an important role in creation of AF substrate in HF. This model is well known to harbor atrial fibrosis. Experiments were conducted during development of embodiments herein to demonstrate that targeted inhibition of NOX2 in HF atrium would prevent atrial fibrosis. In 3 animals, 5-10 mg of NOX2 shRNA was injected sub-epicardially in the posterior left atrium, followed by electroporation. 5 animals underwent injection of pUBc-LacZ (i.e. HF controls). Rapid ventricular pacing was then performed at 240 bpm for 3 weeks, followed by open-chest mapping. Left atrium was examined for NOX2 knockdown (PCR, western blot) and % fibrosis. AF was significantly decreased (NOX2 shRNA vs LacZ=636±151 vs 6±0.6 seconds; p<0.01). There was >50% knockdown of native NOX2 in PLA of NOX2 shRNA vs LacZ dogs (FIG. 6; p<0.01). FIG. 7 shows that fibrosis (stained blue, arrows) was significantly decreased in NOX2 shRNA vs LacZ injected PLA (8.4±0.5% vs 18.8±1.5%, p<0.05). Conclusions: NOX2 shRNA reduces atrial fibrosis in HF.

Example 6

NOX2 shRNA±$G\alpha_{i/o}$-Ct Reverses Electrical Remodeling in RAP

Figure 8:
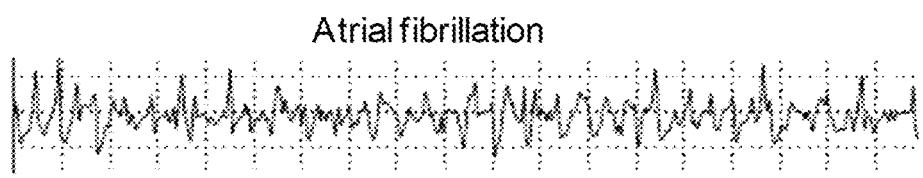
FIG. 8. NOX2 shRNA±G$\alpha$i/o converts AF to flutter or sinus. See text for discussion.
Figure 8:
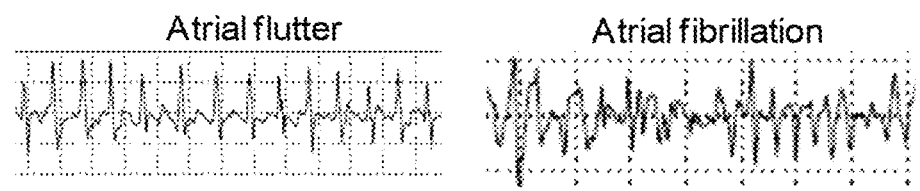
Figure 8:
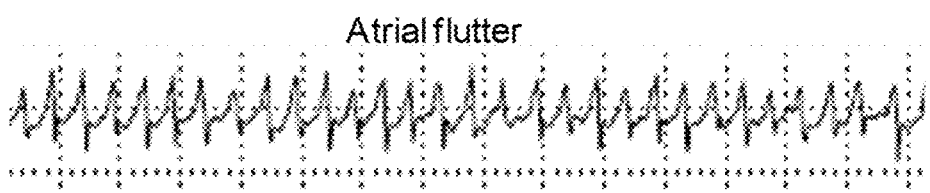
Figure 8:
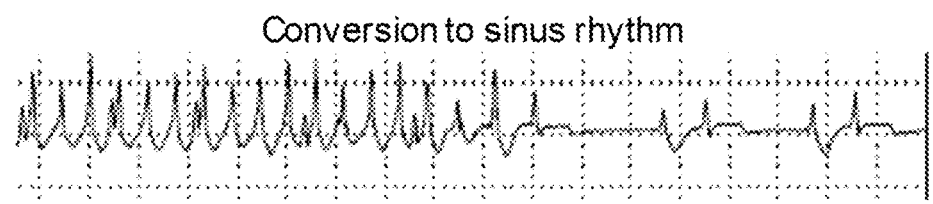

Gene injection after onset of sustained/persistent AF was performed in four animals. All dogs were first subjected to RAP for 2-4 months, so as to obtain advanced electrical remodeling and persistent AF. The dogs were then injected with the following genes: a) NOX2 shRNA (N=1); b) NOX2 shRNA+$G\alpha_{i/o}$-ct (N=2); c) scrambled shRNA (N=1) (FIG. 8). The animal receiving scrambled shRNA continued to be in AF throughout the three-month follow up period after gene injection. The dog receiving NOX2 shRNA alone organized into atrial flutter a few weeks after gene injection, but continued to have paroxysms of AF. Of the two dogs that received NOX2 shRNA+$G\alpha_{i/o}$-ct, one dog converted to atrial flutter a few weeks after gene injection; this dog remained in flutter, with no paroxysms of AF. The other dog that received NOX2 shRNA+$G\alpha_{i/o}$-ct spontaneously converted to sinus rhythm two weeks after gene injection (FIG. 8). This dog is still being followed. Targeting of NOX2—with or concomitant targeting of $G\alpha_{i/o}$—reverses electrical remodeling in AF. The conversion to stable atrial flutter and/or sinus rhythm in the dogs that received NOX2 shRNA+$G\alpha_{i/o}$-ct indicates the presence of synergy between these genes.

REFERENCES

The following references, some of which are cited above by number, are herein incorporated by reference in their entireties.

1 Calkins H, Kuck K H, Cappato R, et al. 2012 HRS/EHRA/ECAS Expert Consensus Statement on Catheter and Surgical Ablation of Atrial Fibrillation: recommendations for patient selection, procedural techniques, patient management and follow-up, definitions, endpoints, and research trial design. Europace 2012; 14:528-606.
2. Nademanee K, McKenzie J, Kosar E, et al. A new approach for catheter ablation of atrial fibrillation: mapping of the electrophysiologic substrate. J Am Coll Cardiol 2004; 43:2044-53.
3. Nademanee K, Schwab M C, Kosar E M, et al. Clinical outcomes of catheter substrate ablation for high-risk patients with atrial fibrillation. Journal of the American College of Cardiology 2008; 51:843-9.
4. Estner H L, Hessling G, Ndrepepa G, et al. Electrogram-guided substrate ablation with or without pulmonary vein isolation in patients with persistent atrial fibrillation. Europace 2008; 10:1281-7.
5. Rahman F, Kwan G F, Benjamin E J. Global epidemiology of atrial fibrillation. Nat Rev Cardiol 2016; 13:501.
6. Chugh S S, Havmoeller R, Narayanan K, et al. Worldwide epidemiology of atrial fibrillation: a Global Burden of Disease 2010 Study. Circulation 2014; 129:837-47.
7. Kirchhof P, Calkins H. Catheter ablation in patients with persistent atrial fibrillation. Eur Heart J 2017; 38:20-6.
8. Ng J, Villuendas R, Cokic I, et al. Autonomic remodeling in the left atrium and pulmonary veins in heart failure: creation of a dynamic substrate for atrial fibrillation. Circ Arrhythm Electrophysiol 2011; 4:388-96.
9. Koduri H, Ng J, Cokic I, et al. Contribution of fibrosis and the autonomic nervous system to atrial fibrillation electrograms in heart failure. Circ Arrhythm Electrophysiol 2012; 5:640-9.
10. Arora R, Ng J, Ulphani J, et al. Unique autonomic profile of the pulmonary veins and posterior left atrium. J Am Coll Cardiol 2007; 49:1340-8.
11. Kunamalla A, Ng J, Parini V, et al. Constitutive Expression of a Dominant-Negative TGF-beta Type II Receptor in the Posterior Left Atrium Leads to Beneficial Remodeling of Atrial Fibrillation Substrate. Circ Res 2016; 119:69-82.
12. Aistrup G L, Cokic I, Ng J, et al. Targeted nonviral gene-based inhibition of Galpha(i/o)-mediated vagal signaling in the posterior left atrium decreases vagal-induced atrial fibrillation. Heart Rhythm 2011; 8:1722-9.
13. Avitall B, Bi J, Mykytsey A, Chicos A. Atrial and ventricular fibrosis induced by atrial fibrillation: evidence to support early rhythm control. Heart Rhythm 2008; 5:839-45.
14. Kim Y M, Guzik T J, Zhang Y H, et al. A myocardial Nox2 containing NAD(P)H oxidase contributes to oxidative stress in human atrial fibrillation. Circ Res 2005; 97:629-36.
15. Arora R. Recent insights into the role of the autonomic nervous system in the creation of substrate for atrial fibrillation: implications for therapies targeting the atrial autonomic nervous system. Circ Arrhythm Electrophysiol 2012; 5:850-9.
16. Yoo S G G, Wren L, Aistrup G, Ng J, Gordon D, Passman R, Knight B, Goldberger J, Arora R. Selective inhibition of parasympathetic nerve signaling by novel C-terminal Gαi/o peptides prevents electrical remodeling induced atrial fibrillation Heart Rhythm 2016; 13:S200.
17. Camm A J. Hopes and disappointments with antiarrhythmic drugs. Int J Cardiol 2017; 237:71-4.
18. Ben Morrison T, Jared Bunch T, Gersh B J. Pathophysiology of concomitant atrial fibrillation and heart failure: implications for management. Nat Clin Pract Cardiovasc Med 2009; 6:46-56.
19. Gillinov A M, Saltman A E. Ablation of atrial fibrillation with concomitant cardiac surgery. Semin Thorac Cardiovasc Surg 2007; 19:25-32.
20. Rahman F, Kwan G F, Benjamin E J. Global epidemiology of atrial fibrillation. Nat Rev Cardiol 2014; 11:639-54.
21. Guerra F, Matassini M V, Scappini L, Urbinati A, Capucci A. Intravenous vernakalant for the rapid conversion of recent onset atrial fibrillation: systematic review and meta-analysis. Expert Rev Cardiovasc Ther 2014; 12:1067-75.
22. Naccarelli G V, Kowey P R. The role of dronedarone in the treatment of atrial fibrillation/flutter in the aftermath of PALLAS. Curr Cardiol Rev 2014; 10:303-8.
23. Andrade J G, Khairy P, Guerra P G, et al. Efficacy and safety of cryoballoon ablation for atrial fibrillation: a systematic review of published studies. Heart Rhythm 2011; 8:1444-51.
24. Providencia R, Marijon E, Combes S, et al. Higher contact-force values associated with better mid-term outcome of paroxysmal atrial fibrillation ablation using the SmartTouch catheter. Europace 2014.
25. Narayan S M, Baykaner T, Clopton P, et al. Ablation of rotor and focal sources reduces late recurrence of atrial fibrillation compared with trigger ablation alone: extended follow-up of the CONFIRM trial (Conventional Ablation for Atrial Fibrillation With or Without Focal Impulse and Rotor Modulation). J Am Coll Cardiol 2014; 63:1761-8.
26. Haissaguerre M, Hocini M, Denis A, et al. Driver domains in persistent atrial fibrillation. Circulation 2014; 130:530-8.
27. Schotten U, Verheule S, Kirchhof P, Goette A. Pathophysiological mechanisms of atrial fibrillation: a translational appraisal. Physiol Rev 2011; 91:265-325.
28. Zsebo K, Yaroshinsky A, Rudy J J, et al. Long-term effects of AAV1/SERCA2a gene transfer in patients with severe heart failure: analysis of recurrent cardiovascular events and mortality. Circ Res 2014; 114:101-8.
29. Jessup M, Greenberg B, Mancini D, et al. Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure. Circulation 2011; 124:304-13.
30. Jaski B E, Jessup M L, Mancini D M, et al. Calcium upregulation by percutaneous administration of gene therapy in cardiac disease (CUPID Trial), a first-in-human phase ½ clinical trial. Journal of cardiac failure 2009; 15:171-81.
31. Chung E S, Miller L, Patel A N, et al. Changes in ventricular remodelling and clinical status during the year following a single administration of stromal cell-derived factor-1 non-viral gene therapy in chronic ischaemic heart failure patients: the STOP-H F randomized Phase II trial. Eur Heart J 2015; 36:2228-38.
32. Penn M S, Mendelsohn F O, Schaer G L, et al. An open-label dose escalation study to evaluate the safety of administration of nonviral stromal cell-derived factor-1 plasmid to treat symptomatic ischemic heart failure. Circ Res 2013; 112:816-25.
33. Su C H, Wu Y J, Wang H H, Yeh H I. Nonviral gene therapy targeting cardiovascular system. Am J Physiol Heart Circ Physiol 2012; 303:H629-38.
34. Bikou O, Thomas D, Trappe K, et al. Connexin 43 gene therapy prevents persistent atrial fibrillation in a porcine model. Cardiovasc Res 2011; 92:218-25.

35. Page R L, Connolly S J, Crijns H J, et al. Rhythm- and rate-controlling effects of dronedarone in patients with atrial fibrillation (from the ATHENA trial). Am J Cardiol 2011; 107:1019-22.
36. Boersma L V, van der Voort P, Debruyne P, et al. Multielectrode Pulmonary Vein Isolation Versus Single Tip Wide Area Catheter Ablation for Paroxysmal Atrial Fibrillation: A Multinational Multicenter Randomized Clinical Trial. Circ Arrhythm Electrophysiol 2016; 9: e003151.
37. Arora R, Ulphani J S, Villuendas R, et al. Neural substrate for atrial fibrillation: implications for targeted parasympathetic blockade in the posterior left atrium. Am J Physiol Heart Circ Physiol 2008; 294:H134-44.
38. Aistrup G L, Villuendas R, Ng J, et al. Targeted G-protein inhibition as a novel approach to decrease vagal atrial fibrillation by selective parasympathetic attenuation. Cardiovasc Res 2009; 83:481-92.
39. Wehr N B, Levine R L. Quantification of protein carbonylation. Methods Mol Biol 2013; 965:265-81.
40. Zakkar M, Ascione R, James A F, Angelini G D, Suleiman M S. Inflammation, oxidative stress and postoperative atrial fibrillation in cardiac surgery. Pharmacol Ther 2015; 154:13-20.
41. Hyde S C, Pringle I A, Abdullah S, et al. CpG-free plasmids confer reduced inflammation and sustained pulmonary gene expression. Nature biotechnology 2008; 26:549-51.
42. Ulphani J S, Arora R, Cain J H, et al. The ligament of Marshall as a parasympathetic conduit. Am J Physiol Heart Circ Physiol 2007; 293:H1629-35.
43. Soucek R, Thomas D, Kelemen K, et al. Genetic suppression of atrial fibrillation using a dominant-negative ether-a-go-go-related gene mutant. Heart Rhythm 2012; 9:265-72.
44. Trappe K, Thomas D, Bikou 0, et al. Suppression of persistent atrial fibrillation by genetic knockdown of caspase 3: a pre-clinical pilot study. Eur Heart J 2013; 34:147-57.
45. Shin Yoo, Anna Pfenniger, Jacob Hoffman, Wenwei Zhang, Jason Ng, Amy Burrell, David A. Johnson, Georg Gussak, Trent Waugh, Suzanne Bull, Brandon Benefield, Bradley P. Knight, Rod Passman, J. Andrew Wasserstrom, Gary L. Aistrup, Rishi Arora. Disruption of NOX2-dependent Oxidative Injury with a Targeted Gene-Therapy Approach Prevents Atrial Fibrillation in a Canine Model. doi: https://doi.org/10.1101/765008 https://t.co/NGIIa43U5i#biorxiv_physio

```
SEQUENCES
SEQ ID NO: 1 (exemplary NOX2 target sequence)-
TATCCATTTCCAAGTCATAGG SEQ ID NO: 2 (exemplary expression vector encoding NOX2 shRNANOX2 shNRA)-
aatgtagtcttatgcaatactcttgtagtcttgcaacatggtaacgatgagttagcaacatgccttacaaggagagaaaa agcaccg tgcatgccgattggtggaagtaaggtggtacgatcgtgccttattaggaaggcaacagacgggtctgacatgg attggacgaacca ctgaattgccgcattgcagagatattgtatttaagtgcctagctcgatacataaacgggtctctctg gttagaccagatctgagcctg ggagctctctggctaactagggaacccactgcttaagcctcaataaagcttgccttgag tgcttcaagtagtgtgtgcccgtctgttgt gtgactctggtaactagagatccctcagacccttttagtcagtgtggaaa atctctagcagtggcgcccgaacagggacttgaaagc gaaagggaaaccagaggagctctctcgacgcaggactcggctt gctgaagcgcgcacggcaagaggcgagggcggcgactgg tgagtacgccaaaaattttgactagcggaggctagaagga gagagatgggtgcgagagcgtcagtattaagcgggggagaatta gatcgcgatgggaaaaaattcggttaaggccagggg gaaagaaaaaatataaattaaaacatatagtatgggcaagcagggagc tagaacgattcgcagttaatcctggcctgtta gaaacatcagaaggctgtagacaaatactgggacagctacaaccatcccttcaga caggatcagaagaacttagatcatt atataatacagtagcaaccctctattgtgtgcatcaaaggatagagataaaagacaccaag gaagctttagacaagatag aggaagagcaaaacaaaagtaagaccaccgcacagcaagcggccgctgatcttcagacctggagg aggagatatgaggga caattggagaagtgaattatataaatataaagtagtaaaaattgaaccattaggagtagcacccaccaag gcaaagagaa gagtggtgcagagagaaaaagagcagtgggaataggagctttgttccttgggttcttgggagcagcaggaagc actatg ggcgcagcgtcaatgacgctgacggtacaggccagacaattattgtctggtatagtgcagcagcagaacaatttgctgag ggctattgaggcgcaacagcatctgttgcaactcacagtctggggcatcaagcagctccaggcaagaatcctggctgtgg aaagat acctaaaggatcaacagctcctggggatttggggttgctctggaaaactcatttgcaccactgctgtgccttgg aatgctagttggag taataaatctctggaacagatttggaatcacacgacctggatggagtgggacagagaaattaacaa ttacacaagcttaatacact ccttaattgaagaatcgcaaaaccagcaagaaaagaatgaacaagaattattggaattag ataaatgggcaagtttgtggaattgg tttaacataacaaattggctgtggtatataaaattattcataatgatagtagga ggcttggtaggtttaagaatagttttgctgtactt tctatagtgaatagagttaggcagggatattcaccattatcgtt tgagacccacctcccaacccgaggggacccgacaggcccga aggaatagaagaagaaggtggagagagagacagagaca gatccattcgattagtgaacggatctcgacggtatcgatcacgaga ctagcctcgacggccgcccccttcaccagggc ctatttcccatgattccttcatatttgcatatacgatacaaggctgttagagag ataattggaatttaatttgactgtaaa cacaaagatattagtacaaaatacgtgacgtagaaagtaataatttcttgggtagtttgcag
```

-continued

```
ttttaaaattatgttttta  aaatggactatcatatgcttaccgtaacttgaaagtatttcgatttcttggctttatatatcttgtggaaagga
cgaaac  accggtacaacagccacaacgtctatctcgagatagacgttgtggctgttgtattttgaattctcgacctcgagacaaa t
ggcagtattcatccacaattttaaaagaaaaggggggattgggggtacagtgcaggggaaagaatagtagacataata  gcaac
agacatacaaactaaagaattacaaaaacaaattacaaaaattcaaaattttcgggtttattacagggacagcag  agatccactttg
gccgcggctcgaggggggttggggttgcgccttttccaaggcagccctgggtttgcgcagggacgcggc  tgctctgggcgtggttccg
ggaaacgcagcggccgcgaccctgggtctcgcacattcttcacgtccgttcgcagcgtcac  ccggatcttcgccgctaccttgtgg
gcccccggcgacgcttcctgctccgccctaagtcgggaaggttccttgcggt  tcgcggcgtgccggacgtgacaaacggaagcc
gcacgtctcactagtaccctcgcagacggacagcgccagggagcaatg  gcagcgcgccgaccgcgatgggctgtggccaatagc
ggctgctcagcagggcgcgccgagagcagcggccgggaagggc  ggtgcgggaggcgggtgtggggcggtagtgtgggccct
gttcctgcccgcgcggtgttccgcattctgcaagcctccgg  agcgcacgtcggcagtcggctccctcgttgaccgaatcaccgacctc
tctccccaggggatccaccggagcttaccatg  accgagtacaagcccacggtgcgcctcgccacccgcgacgacgtccccaggg
ccgtacgcaccctcgccgccgcgttcgc  cgactaccccgccacgcgccacaccgtcgatccggaccgccacatcgagcgggtcacc
gagctgcaagaactcttcctca  cgcgcgtcgggctcgacatcggcaaggtgtgggtcgcggacgacggcgccgcggtggcggtct
ggaccacgccggagagc  gtcgaagcgggggcggtgttcgccgagatcggccgcgcatggccgagttgagcggttcccggctgg
ccgagcagcaaca  gatggaaggcctcctggcgccgcaccggcccaaggagcccgcgtggttcctggccaccgtcggcgtctcgcc
cgaccacc  agggcaagggtctgggcagcgccgtcgtgctccccggagtggaggcggccgagcgcgccggggtgcccgccttcctg
gag  acctccgcgcccgcaacctcccttctacgagcggctcggcttcaccgtcaccgccgacgtcgaggtgcccgaaggacc  gc
gcacctggtgcatgacccgcaagcccggtgcctgacgcccgcccacgaccccgcagcgcccgaccgaaaggagcgcac  gacccc
atgcatcggtacctttaagaccaatgacttacaaggcagctgtagatcttagccactttttaaaagaaaagggg  ggactggaaggg
ctaattcactcccaacgaagacaagatctgcttttttgcttgtactgggtctctctggttagaccagat  ctgagcctgggagctctctgg
ctaactagggaacccactgcttaagcctcaataaagcttgccttgagtgcttcaagtag  tgtgtgcccgtctgttgtgtgactctggta
actagagatccctcagaccctttagtcagtgtggaaaatctctagcagt  agtagttcatgtcatcttattattcagtatttataacttgc
aaagaaatgaatatcagagagtgagaggaacttgtttat  tgcagcttataatggttacaaataaagcaatagcatcacaaatttcac
aaataaagcatttttttcactgcattctagtt  gtggtttgtccaaactcatcaatgtatcttatcatgtctggctctagctatcccgcccct
aactccgcccatcccgcccc  taactccgcccagttccgcccattctccgccccatggctgactaatttttttatttatgcagaggccga
ggccgcctcg  gcctctgagctattccagaagtagtgaggaggcttttttggaggcctagggacgtacccaattcgccctatagtgag
tcg  tattacgcgcgctcactggccgtcgttttacaacgtcgtgactgggaaaaccctggcgttacccaacttaatcgccttgc  agcac
atccccctttcgccagctggcgtaatagcgaagaggcccgcaccgatcgcccttcccaacagttgcgcagcctga  atggcgaatgg
gacgcgccctgtagcggcgcattaagcgcggcgggtgtggtggttacgcgcagcgtgaccgctacactt  gccagcgccctagcgcc
cgctcctttcgctttcttcccttcctttctcgccacgttcgccggctttccccgtcaagctct  aaatcggggggctcccttttagggttccgat
ttagtgctttacggcacctcgaccccaaaaaacttgattagggtgatggtt  cacgtagtgggccatcgccctgatagacggttttttcg
ccctttgacgttggagtccacgttctttaatagtggactcttg  ttccaaactggaacaacactcaaccctatctcggtctattcttttgat
ttataagggattttgccgatttcggcctattg  gttaaaaaatgagctgatttaacaaaaatttaacgcgaattttaacaaaatattaac
gcttacaatttaggtggcacttt  tcggggaaatgtgcgcggaacccctatttgtttattttttctaaatacattcaaatatgtatccgctca
tgagacaataac  cctgataaatgcttcaataatattgaaaaaggaagagtatgagtattcaacatttccgtgtcgcccttattcccttt
ttt  gcggcattttgccttcctgtttttgctcacccagaaacgctggtgaaagtaaaagatgctgaagatcagttgggtgcacg  agtgg
gttacatcgaactggatctcaacagcggtaagatccttgagagttttcgccccgaagaacgttttccaatgatga  gcacttttaaagtt
ctgctatgtggcgcggtattatcccgtattgacgccgggcaagagcaactcggtcgccgcatacac  tattctcagaatgacttggttg
agtactcaccagtcacagaaaagcatcttacggatggcatgacagtaagagaattatg  cagtgctgccataaccatgagtgataac
actgcggccaacttacttctgacaacgatcggaggaccgaaggagctaaccg  cttttttgcacaacatgggggatcatgtaactcgc
```

-continued cttgatcgttgggaaccggagctgaatgaagccataccaaacgac gagcgtgacaccacgatgcctgtagcaatggcaacaacgg tgcgcaaactattaactggcgaactacttactctagcttc ccggcaacaattaatagactggatggaggcggataaagttgcaggac cacttctgcgctcggcccttccggctggctggt ttattgctgataaatctggagccggtgagcgtgggtctcgcggtatcattgcagca ctggggccagatggtaagccctcc cgtatcgtagttatctacacgacggggagtcaggcaactatggatgaacgaaatagacagat cgctgagataggtgcctc actgattaagcattggtaactgtcagaccaagtttactcatatatactttagattgatttaaaacttcattt ttaattta aaaggatctaggtgaagatcctttttgataatctcatgaccaaaatcccttaacgtgagttttcgttccactgagcgtcag accccgtagaaaagatcaaggatcttcttgagatcctttttttctgcgcgtaatctgctgcttgcaaacaaaaaaacc accgctacc agcggtggtttgtttgccggatcaagagctaccaactctttttccgaaggtaactggcttcagcagagcgc agataccaaatactgtt cttctagtgtagccgtagttaggccaccacttcaagaactctgtagcaccgcctacatacctc gctctgctaatcctgttaccagtggc tgctgcagttggcgataagtcgtgtcttaccgggttggactcaagacgatagtt accggataaggcgcagcggtcgggctgaacgg ggggttcgtgcacacagcccagcttggagcgaacgacctacaccgaac tgatacctacagcgtgagctatgagaaagcgccac gcttcccgaagggagaaaggcggacaggtatcaggtaagcggc agggtcggaacaggagagcgcacgagggagcttccagggg gaaacgcctggtatctttatagtcctgtcgggtttcgcca cctctgacttgagcgtcgattttgtgatgctcgtcagggggcggagc ctatggaaaaacgccagcaacgcggccttt tacggttcctggccttttgctggcttttgctcacatgttctttcctgcgttatccctg attctgtggataaccgtatt accgcctttgagtgagctgataccgctcgccgcagccaacgaccgagcgcagcgagtcagtgagc gaggaagcggaaga gcgcccaatacgcaaaccgcctctccccgcgcgttggccgattcattaatgcagctggcacgacaggtttcc cgactgga aagcgggcagtgagcgcaacgcaattaatgtgagttagctcactcattaggcaccccaggctttacactttatgcttcc g gctcgtatgttgtgtggaattgtgagcggataacaatttcacacaggaaacagctatgaccatgattacgccaagcgcgc aatta accctcactaaagggaacaaaagctggagctgcaagctt SEQ ID NO: 3 (exemplary Gα_i inhibitory peptide; C-terminal 11 amino acids of the
Gα_{i2} subunit)-
IKNNLKDCGLF SEQ ID NO: 4 (Gα_o inhibitory peptide; C-terminal 11 amino acids of the Gα_{o1} subunit)-
IANNLRGCGLY SEQ ID NOS: 5-19 (exemplary G-protein inhibitory peptides)-
FIG. 9

SEQ ID NOS: 20-33 (exemplary minigenes encoding G-protein inhibitory peptides)-
FIG. 10

SEQ ID NO: 34 (exemplary NOX2 shRNA) -
CCGCCTATGACTTGGAAATGGATACTCGAGTATCCATTTCCAAGTCATAGGTTTTTG

---

The invention claimed is:

1. A method of reversing cardiac electrical remodeling associated with atrial fibrillation (AF) in a subject suffering from cardiac electrical remodeling associated with atrial fibrillation, comprising co-administering to the subject by directly injecting into the atrium of a subject an effective amount of:
   (a) an inhibitor of NADPH oxidase 2 (NOX2) gene expression selected from a short hairpin RNA (shRNA), a silencing RNA (siRNA), or an antisense RNA; and
   (b) (i) a nucleic acid encoding a C-terminal $G\alpha_i$ inhibitory peptide, and/or
   (ii) a nucleic acid encoding a C-terminal $G\alpha_o$ inhibitory peptide;
to the subject, wherein cardiac electrical remodeling associated with AF is reversed.

2. The method of claim 1, comprising administering a shRNA or siRNA inhibitor of NOX2 gene expression.

3. The method of claim 2, comprising administering a shRNA inhibitor of NOX2 gene expression.

4. The method of claim 2, wherein the NOX2 shRNA comprises SEQ ID NO: 34.

5. The method of claim 1, wherein (a) the inhibitor of NOX2 gene expression and (b) (i) the nucleic acid encoding a C-terminal $G\alpha_i$ inhibitory peptide and/or (ii) the nucleic acid encoding a C-terminal $G\alpha_o$ inhibitory peptide are administered to the myocardial tissue.

6. The method of claim 5, further comprising electroporating the myocardial tissue before, during, or after the administration.

7. The method of claim 1, wherein (a) the inhibitor of NOX2 gene expression and (b) (i) the nucleic acid encoding a C-terminal $G\alpha_i$ inhibitory peptide and/or (ii) the nucleic acid encoding a C-terminal $G\alpha_o$ inhibitory peptide are administered to the endocardium or epicardium.

* * * * *